US008221761B1

(12) United States Patent
Grandi et al.

(10) Patent No.: US 8,221,761 B1
(45) Date of Patent: Jul. 17, 2012

(54) ENHANCEMENT OF BACTERICIDAL ACTIVITY OF NEISSERIA ANTIGENS WITH OLIGONUCLEOTIDES CONTAINING CG MOTIFS

(75) Inventors: Guido Grandi, Milan (IT); Rino Rappuoli, Siena (IT); Marzia M. Giuliani, Siena (IT); Mariagrazia Pizza, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/914,454

(22) PCT Filed: Feb. 9, 2000

(86) PCT No.: PCT/IB00/00176
§ 371 (c)(1),
(2), (4) Date: Jan. 14, 2002

(87) PCT Pub. No.: WO00/50075
PCT Pub. Date: Aug. 31, 2000

(51) Int. Cl.
*A61K 39/00* (2006.01)
*A61K 39/38* (2006.01)
*A61K 45/00* (2006.01)
*A61K 47/00* (2006.01)
*A61K 39/02* (2006.01)
*A61K 39/095* (2006.01)

(52) U.S. Cl. ............... 424/184.1; 424/250.1; 424/234.1; 424/278.1; 424/450; 514/44 R

(58) Field of Classification Search ............... 424/234.1, 424/185.1, 184.1, 249.1, 450, 489, 488, 190.1, 424/484, 250.1, 486, 236.1; 514/44, 2
See application file for complete search history.

(56) References Cited

U.S. PATENT DOCUMENTS

| | | | | |
|---|---|---|---|---|
| 6,299,884 B1 * | 10/2001 | Van Nest et al. | ........... | 424/283.1 |
| 6,451,325 B1 * | 9/2002 | Van Nest et al. | ........... | 424/283.1 |
| 6,544,518 B1 * | 4/2003 | Friede et al. | ............... | 424/184.1 |
| 6,558,670 B1 * | 5/2003 | Friede et al. | ............... | 424/184.1 |
| 6,627,204 B1 * | 9/2003 | Ruelle | ......................... | 424/250.1 |
| 6,709,660 B1 * | 3/2004 | Scarlato et al. | ............. | 424/250.1 |
| 6,753,015 B2 * | 6/2004 | Fang et al. | ..................... | 424/489 |
| 6,770,284 B1 * | 8/2004 | Ruelle | ......................... | 424/250.1 |
| 6,797,273 B1 * | 9/2004 | Ruelle | ......................... | 424/250.1 |
| 6,797,274 B1 * | 9/2004 | Ruelle | ......................... | 424/250.1 |
| 6,855,492 B2 * | 2/2005 | O'Hagan et al. | .................. | 435/4 |
| 6,861,410 B1 * | 3/2005 | Ott et al. | ........................ | 514/26 |
| 7,056,521 B2 * | 6/2006 | Barchfeld et al. | ......... | 424/236.1 |
| 7,314,624 B2 * | 1/2008 | Baker et al. | ................ | 424/192.1 |
| 7,348,006 B2 * | 3/2008 | Contorni et al. | ........... | 424/184.1 |
| 7,368,261 B1 * | 5/2008 | Rappuoli | ..................... | 435/69.1 |
| 7,399,472 B2 * | 7/2008 | Friede et al. | ............... | 424/184.1 |
| 7,504,111 B2 * | 3/2009 | Fontana et al. | ............. | 424/249.1 |
| 7,534,444 B2 * | 5/2009 | Granoff et al. | ............. | 424/250.1 |
| 7,538,207 B2 * | 5/2009 | Rappuoli et al. | ............. | 536/23.7 |
| 7,576,176 B1 * | 8/2009 | Fraser et al. | .................. | 530/350 |
| 7,615,539 B2 * | 11/2009 | Uhlmann et al. | ........... | 514/44 R |
| 7,641,911 B2 * | 1/2010 | Ott et al. | ..................... | 424/283.1 |
| 2001/0044416 A1 * | 11/2001 | McCluskie et al. | ............. | 514/44 |
| 2002/0025326 A1 * | 2/2002 | Blonder et al. | ............. | 424/207.1 |
| 2003/0027907 A1 * | 2/2003 | Morin et al. | ................. | 524/387 |
| 2003/0170273 A1 * | 9/2003 | O'Hagan et al. | ........... | 424/225.1 |
| 2004/0013686 A1 * | 1/2004 | Granoff et al. | ............. | 424/190.1 |
| 2004/0092711 A1 * | 5/2004 | Arico et al. | ..................... | 530/350 |
| 2004/0101537 A1 * | 5/2004 | O'Hagan et al. | ........... | 424/249.1 |
| 2004/0110670 A1 * | 6/2004 | Arico et al. | ..................... | 514/12 |
| 2004/0126391 A1 * | 7/2004 | Scarlato et al. | ............. | 424/190.1 |
| 2004/0202669 A1 * | 10/2004 | O'Hagan | .................... | 424/184.1 |
| 2004/0249125 A1 * | 12/2004 | Pizza et al. | ..................... | 530/350 |
| 2004/0258702 A1 * | 12/2004 | Blonder et al. | ............. | 424/184.1 |
| 2005/0002948 A1 * | 1/2005 | Ryall | ......................... | 424/184.1 |
| 2005/0074450 A1 * | 4/2005 | Giuliani et al. | ............. | 424/132.1 |
| 2005/0075485 A1 * | 4/2005 | Ruelle | .......................... | 530/350 |
| 2007/0082014 A1 * | 4/2007 | Costantino | .................. | 424/250.1 |
| 2008/0026071 A1 * | 1/2008 | O'Hagan et al. | ............. | 424/497 |
| 2008/0171063 A1 * | 7/2008 | Hanon et al. | ................ | 424/209.1 |
| 2008/0181949 A1 * | 7/2008 | Baker et al. | .................. | 424/484 |
| 2008/0193470 A1 * | 8/2008 | Masignani et al. | ........ | 424/185.1 |
| 2008/0254057 A1 * | 10/2008 | Costantino | ............... | 424/197.11 |
| 2008/0311156 A1 * | 12/2008 | Friede et al. | ................ | 424/208.1 |
| 2009/0047306 A1 * | 2/2009 | Nash et al. | .................. | 424/204.1 |
| 2009/0062224 A1 * | 3/2009 | Kim et al. | ........................ | 514/44 |
| 2009/0074851 A1 * | 3/2009 | Bachmann et al. | ........... | 424/450 |
| 2009/0081244 A1 * | 3/2009 | Glenn et al. | ................ | 424/184.1 |
| 2009/0089165 A1 * | 4/2009 | Sweeney | ........................ | 705/14 |
| 2009/0136543 A1 * | 5/2009 | Ballou et al. | ............... | 424/206.1 |
| 2009/0191226 A2 * | 7/2009 | Van Nest et al. | ........... | 424/184.1 |
| 2010/0183667 A1 * | 7/2010 | Ballou et al. | ............... | 424/206.1 |

FOREIGN PATENT DOCUMENTS

| | | |
|---|---|---|
| EP | 399843 A2 * | 5/1990 |
| EP | 822831 B1 * | 2/1998 |
| WO | WO 96/02555 | 2/1996 |
| WO | WO 98/16247 | 4/1998 |
| WO | WO 98/18810 | 5/1998 |
| WO | WO 98/37919 | 9/1998 |
| WO | WO 98/40100 | 9/1998 |

(Continued)

OTHER PUBLICATIONS

Glenn, Expert Reviews Vaccines, 2003, 2/2:163-164.*
Al-Bader, Dissertation Abstracts International, 2002, 64/3C:637.*
Singh et al, J. Pharmaceutical Sciences, Feb. 2004, 93/2:273-282.*
Otto et al, In: Vaccine Design: The Subunit and Adjuvant Approach, editors—Powell et al, 1995, pp. 277-296.*
Mesa et al, Vaccine, 2004, 22:3045-3052.*
Jodar et al, Lancet, Apr. 2002, 359:1499-1508.*

(Continued)

*Primary Examiner* — Nita M Minnifield
(74) *Attorney, Agent, or Firm* — Amy Hessler; Otis Littlefield

(57) ABSTRACT

Immunogenic compositions (e.g. vaccines) comprising: (a) an immunostimulating amount of a *Neisseria* antigen (preferably *N. meningitidis* serogroup B); and (b) an immunostimulating amount of an adjuvant composition comprising an oligonucleotide comprising at least one CG motif. Component (b) may further comprise a second adjuvant. Component (a) may be selected from a variety of antigens. Adjuvant compositions comprising an oligonucleotide having at least one CG motif, and complete Freund's adjuvant (CFA) are also provided.

35 Claims, No Drawings

FOREIGN PATENT DOCUMENTS

| | | |
|---|---|---|
| WO | WO 98/49288 | 11/1998 |
| WO | WO 98/52581 | 11/1998 |
| WO | WO 98/55495 | 12/1998 |
| WO | WO 98/56414 A1 * | 12/1998 |
| WO | WO/99/33488 | 7/1999 |
| WO | WO 99/57280 | 11/1999 |
| WO | WO 99/58683 | 11/1999 |

OTHER PUBLICATIONS

Lefber et al, Infection and Immunity, Dec. 2003, 71/12:6915-6920.*
Christodoulides et al, Vaccine, 2000, 18:131-139.*
Pollard et al, Vaccine, 2001, 19:1327-1346.*
Pizza et al, Science, Mar. 10, 2000, 287:1816-1820.*
Tettelin et al, Science, Mar. 10, 2000, 287:1809-1815.*
Parkhill et al, Nature, Mar. 30, 2000, 404:502-506.*
Gupta et al, Vaccine, 1995, 13/14:1263-1276.*
McNella et al, Advanced Drug Delivery Reviews, 2001, 51:43-54.*
O'Hagan et al, biomolecular Engineering, 2001, 18:69-85.*
Singh et al, International J. Parasitology, 2003, 33:469-478.*
McCluskie et al, Vaccine, 2000, 18:231-237.*
Eriksson et al, Current Opinion in Immunology, 2002, 14:666-672.*
Klinman et al, Immunological Reviews, 2001, 199:201-216.*
Homer et al, Clinical Immunology, Apr. 2000, 95/1:S19-S29.*
Hanes et al, Advanced Drug Delivery Reviews, 1997, 28:97-119.*
Singh et al, Expert Opinion Biol. Ther., 2004, 4/4:483-491.*
Classen et al, Vaccine, 1996, 14/10:1001-1008.*
Gomez et al, Vaccine, 1998, 16/17:1633-1639.*
Al-Bader, Dissertation Abstracts International, 2002, 64/3C:637 abstract only.*
Manmohan et al, Nature Biotechnology, Nov. 1999, 17:1075-1081.*
Freytag et al, Vaccine, 2005, 23:1804-1813.*
Coupland et al, In: Adjuvants Agrichem., 1992, ed. Chester L. Foy, pp. 449-461 abstract only.*
O'Hagan et al, Vaccine, 2002, 20:3389-3398.*
Spickler et al, J. Vet. Intern. Med., 2003, 17:273-281.*
Singh et al, Nature Biotechnology, Nov. 1999, 17:1075-1081.*
Cox et al, Vaccine, 1997, 15/3:248-256.*
Krieg, BioDrugs, 1998, 5:341-346.*
Yamamoto et al, Antisense Research and Development, 1994, 4:119-122.*
Agrawal et al, Trends in Mol. Med., 2002, 8:114-121.*
Hartmann et al, J. Immunology, 2000, 164:1617-1624.*
Weiner, J. Leukocyte Biology, 2000, 68:456-463.*
Agrawal et al, Molecular Med. Today, 2000, 6:72-81.*
Zhao et al, Biochemical Pharmacology, 1996, 51:173-182.*
Saukkonen et al, Vaccine, 1989, 7/4:325-328.*
Jennings et al, J. Immunology, May 15, 1989, 142/10:3585-3591.*
Jordens et al, Infection and Immunity, Nov. 2004, 72/11:6503-6510.*
Malyala et al, J. Pharmaceutical Sciences, Mar. 2008, 97/3:1155-1164.*
Ballas et al., "Induction of NK Activity in Murine and Human Cells by CpG Motifs in Oligodeoxynucleotides and Bacterial DNA," *J. Immunol.*, 157:1840-1845 (1996).
Bird, "CpG Islands As Gene Markers In The Vertebrate Nucleus," *Trends Genet.*, 3:342-347(1987).
Chu et al., "CpG Oligodeoxynucleotides Act As Adjuvants That Switch On T Helper 1 (Th1) Immunity," *J. Exp. Med.*,186:1623-1631 (1997).
Cowdery et al., "Bacterial DNA Induces NK Cells to Produce IFN-γ In Vivo and Increases the Toxicity of Lipopolysaccharides," *J. Immunol.*, 156:4570-4575 (1996).
Davis et al., "CpG DNA Is a Potent Enhancer of Specific Immunity in Mice Immunized with Recombinant Hepatitis B Surface Antigen," *J. Immunol*, 160:870-876 (1998).
Halpern et al.,"Bacterial DNA Induces Murine Interferon-γ Production by Stimulation of Interleukin-12 and Tumor Necrosis Factor-α ," *Cell. Immunol*, 167:72-78 (1996).
Klinman et al, "CpG motifs present in bacterial DNA rapidly induce lymphocytes to secrete interleukin 6, interleukin 12, and interferon γ," *Proc. Natl. Acad. Sci. USA*, 93:2879-2883 (1996).
Krieg et al., "CpG motifs in bacterial DNA trigger direct B-cell activation," *Nature*, 374:546-549, (1995).
Lipford et al, "CpG-containing synthetic oligonucleotides promote B and Cytotoxic T cell responses to protein antigen: a new class of vaccine adjuvants," *Eur. J. Immunol.*, 27:2340-2344 (1997).
Messina et al, "Stimulation of In Vitro Murine Lymphocyte Proliferation by Bacterial DNA," *J. Immunol.*, 147:1759-1764 (1991).
Millan et al.,"CpG DNA can induce strong Th1 humoral and cell-mediated immune responses against hepatitis B surface antigen in young mice," *Proc. Natl. Acad. Sci*, 95:15553-15558 (1998).
Moldoveanu et al, "CpG DNA, a novel immune enhancer for systemic and mucosal immunization with influenza virus," *Vaccine*, 16:1216-1224 (1988).
Roman et al.,"Immunostimulatory DNA sequences function as T helper-1-promoting adjuvants," *Nat. Med.*, 3:849-854 (1997).
Stacey et al., "Macrophages Ingest and Are Activated by Bacterial DNA," *J. Immunol.*, 157:2116-2122 (1996).
Sun et al., "DNA as an Adjuvant: Capacity of Insect DNA and Synthetic Oligodeoxynucleotides to Augment T Cell Responses to Specific Antigen," *J. Exp. Med*, 187:1145-1150,(1998).
Weiner et al., "Immunostimulatory oligodeoxynucleotides containing the CpG motif are effective as immune adjuvants in tumor antigen immunization," *Proc. Natl. Acad. Sci. USA*, 94:10833-10837 (1997).
Yamamoto et al, and Production of In vitro Augmentation of Natural Killer Cell Activity Interferon-α/β and -γ with Deoxyribonucleic Acid Fraction from *Mycobacterium bovis* BCG *Jpn. J. Cancer Res.*, 79:866-873 (1988).
Yi et al., "CpG DNA Rescue of Murine B Lymphoma Cells from Anti-IgM-Induced Growth Arrest and Programmed Cell Death Is Associated with Increased Expression of c-*myc* and bcl-$x_L^{1,2}$," *J. Immunol.*, 157:4918-4925 (1996).
Yi et al., "CpG Motifs in Bacterial DNA Activate Leukocytes Through the pH-Dependent Generation of Reactive Oxygen Species," *J. Immunol.*, 160:4755-4761 (1998).
Yi et al., "CpG Oligodeoxyribonucleotides Rescue Mature Spleen B Cells from Spontaneous Apoptosis and Promote Cell Cycle Entry," *J. Immunol.*, 160:5898-5906 (1998).
Yi et al., "Rapid Immune Activation by CpG Motifs in Bacterial DNA," *J. Immunol.*, 157:5394-5402 (1996).
Aucouturier et al. (2001). "Adjuvants designed for veterinary and human vaccines," *Vaccine* 19:2666-2672.
Edelman (2002). "The Development and Use of Vaccine Adjuvants," *Molecular Biotechnology* 21(2):129-148.
Wuorimaa et al. (2001). "Avidity and Subclasses of IgG after Immunization of Infants with an 11-Valent Pneumococcal Conjugate Vaccine with or without Aluminum Adjuvant," *The Journal of Infectious Disease* 184:1211-5.

* cited by examiner

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 1
tccatgacgt tcctgacgtt                                                 20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 2
ataatcgacg ttcaagcaag                                                 20

<210> SEQ ID NO 3
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 3
ggggtcaacg ttgagggggg                                                 20

<210> SEQ ID NO 4
<211> LENGTH: 18
```

```
<212> TYPE: DNA
<213> ORGANISM: Artificial Sequence
<220> FEATURE:
<223> OTHER INFORMATION: oligonucleotide adjuvant

<400> SEQUENCE: 4
tctcccagcg tgcgccat                                               18

<210> SEQ ID NO 5
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 5
gagaacgctc gaccttcgat                                             20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 6
tccatgtcgt tcctgatgct                                             20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 7
tccatgacgt tcctgatgct                                             20

<210> SEQ ID NO 8
<211> LENGTH: 15
<212> TYPE: DNA
<213> ORGANISM: Artificial Sequence
<220> FEATURE:
<223> OTHER INFORMATION: oligonucleotide adjuvant

<400> SEQUENCE: 8
gctagacgtt agcgt                                                  15

<210> SEQ ID NO 9
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 9
atcgactctc gagcgttctc                                             20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide adjuvant

<400> SEQUENCE: 10
gaaccttcca tgctgttccg                                             20
```

```
<210> SEQ ID NO 11
<211> LENGTH: 15
<212> TYPE: DNA
<213> ORGANISM: Artificial Sequence
<220> FEATURE:
<223> OTHER INFORMATION: oligonucleotide adjuvant

<400> SEQUENCE: 11
gctagatgtt agcgt                                                           15

<210> SEQ ID NO 12
<211> LENGTH: 8
<212> TYPE: DNA
<213> ORGANISM: Artificial Sequence
<220> FEATURE:
<223> OTHER INFORMATION: oligonucleotide adjuvant

<400> SEQUENCE: 12 tcaacgtt                                                                    8

<210> SEQ ID NO 13
<211> LENGTH: 8
<212> TYPE: DNA
<213> ORGANISM: Artificial Sequence
<220> FEATURE:
<223> OTHER INFORMATION: oligonucleotide adjuvant

<400> SEQUENCE: 13 gcaacgtt                                                                    8

<210> SEQ ID NO 14
<211> LENGTH: 8
<212> TYPE: DNA
<213> ORGANISM: Artificial Sequence
<220> FEATURE:
<223> OTHER INFORMATION: oligonucleotide adjuvant

<400> SEQUENCE: 14 tcgacgtc                                                                    8

<210> SEQ ID NO 15
<211> LENGTH: 8
<212> TYPE: DNA
<213> ORGANISM: Artificial Sequence
<220> FEATURE:
<223> OTHER INFORMATION: oligonucleotide adjuvant

<400> SEQUENCE: 15 tcagcgct                                                                    8

<210> SEQ ID NO 16
<211> LENGTH: 8
<212> TYPE: DNA
<213> ORGANISM: Artificial Sequence
<220> FEATURE:
<223> OTHER INFORMATION: oligonucleotide adjuvant

<400> SEQUENCE: 16 tcaacgct                                                                    8

<210> SEQ ID NO 17
<211> LENGTH: 8
<212> TYPE: DNA
<213> ORGANISM: Artificial Sequence
<220> FEATURE:
<223> OTHER INFORMATION: oligonucleotide adjuvant
```

```
<400> SEQUENCE: 17 tcatcgat                                                          8

<210> SEQ ID NO 18
<211> LENGTH: 8
<212> TYPE: DNA
<213> ORGANISM: Artificial Sequence
<220> FEATURE:
<223> OTHER INFORMATION: oligonucleotide adjuvant

<400> SEQUENCE: 18 tcttcgaa                                                          8

<210> SEQ ID NO 19
<211> LENGTH: 22
<212> TYPE: DNA
<213> ORGANISM: Artificial Sequence
<220> FEATURE:
<223> OTHER INFORMATION: oligonucleotide adjuvant

<400> SEQUENCE: 19
tgactgtgaa cgttcgagat ga                                         22

<210> SEQ ID NO 20
<211> LENGTH: 22
<212> TYPE: DNA
<213> ORGANISM: Artificial Sequence
<220> FEATURE:
<223> OTHER INFORMATION: oligonucleotide adjuvant

<400> SEQUENCE: 20
tgactgtgaa cgttagcgat ga                                         22

<210> SEQ ID NO 21
<211> LENGTH: 22
<212> TYPE: DNA
<213> ORGANISM: Artificial Sequence
<220> FEATURE:
<223> OTHER INFORMATION: oligonucleotide adjuvant

<400> SEQUENCE: 21
tgactgtgaa cgttagagcg ga                                         22

<210> SEQ ID NO 22
<211> LENGTH: 22
<212> TYPE: DNA
<213> ORGANISM: Artificial Sequence
<220> FEATURE:
<223> OTHER INFORMATION: oligonucleotide adjuvant

<400> SEQUENCE: 22
gtttgcgcaa cgttgttgcc at                                         22

<210> SEQ ID NO 23
<211> LENGTH: 22
<212> TYPE: DNA
<213> ORGANISM: Artificial Sequence
<220> FEATURE:
<223> OTHER INFORMATION: oligonucleotide adjuvant

<400> SEQUENCE: 23
atggcaacaa cgttgcgcaa ac                                         22

<210> SEQ ID NO 24
<211> LENGTH: 22
```

```
<212> TYPE: DNA
<213> ORGANISM: Artificial Sequence
<220> FEATURE:
<223> OTHER INFORMATION: oligonucleotide adjuvant

<400> SEQUENCE: 24
cattggaaaa cgttcttcgg gg                                              22

<210> SEQ ID NO 25
<211> LENGTH: 22
<212> TYPE: DNA
<213> ORGANISM: Artificial Sequence
<220> FEATURE:
<223> OTHER INFORMATION: oligonucleotide adjuvant

<400> SEQUENCE: 25
ccccgaagaa cgttttccaa tg                                              22

<210> SEQ ID NO 26
<211> LENGTH: 12
<212> TYPE: DNA
<213> ORGANISM: Artificial Sequence
<220> FEATURE:
<223> OTHER INFORMATION: oligonucleotide adjuvant

<400> SEQUENCE: 26
attgacgtca at                                                         12

<210> SEQ ID NO 27
<211> LENGTH: 22
<212> TYPE: DNA
<213> ORGANISM: Artificial Sequence
<220> FEATURE:
<223> OTHER INFORMATION: oligonucleotide adjuvant

<400> SEQUENCE: 27
ctttccattg acgtcaatgg gt                                              22

<210> SEQ ID NO 28
<211> LENGTH: 33
<212> TYPE: DNA
<213> ORGANISM: Artificial Sequence
<220> FEATURE:
<223> OTHER INFORMATION: Forward primer from example 2

<400> SEQUENCE: 28
cgcggatccc atatgtgcca aagcaagagc atc                                  33

<210> SEQ ID NO 29
<211> LENGTH: 25
<212> TYPE: DNA
<213> ORGANISM: Reverse primer from example 2

<400> SEQUENCE: 29
cccgctcgag cgggcggtat tcggg                                           25

<210> SEQ ID NO 30
<211> LENGTH: 1326
<212> TYPE: DNA
<213> ORGANISM: Neisseria meningitidis

<400> SEQUENCE: 30
atgaaaaaat accctattccg cgccgccctg tacggcatcg ccgccgccat cctcgccgcc     60
tgccaaagca agagcatcca aacctttccg caacccgaca catccgtcat caacggcccg    120
gaccggccgg tcggcatccc cgaccccgcc ggaacgacgg tcgcggcgg cggggccgtc    180
```

```
tataccgttg taccgcacct gtccctgccc cactgggcgg cgcaggattt cgccaaaagc    240
ctgcaatcct tccgcctcgg ctgcgccaat ttgaaaaacc gccaaggctg caggatgtg     300 tgcgcccaag cctttcaaac ccccgtccat tcctttcagg caaaacagtt ttttgaacgc    360
tatttcacgc cgtggcaggt tgcaggcaac ggaagccttg ccggtacggt taccggctat    420
tacgaaccgg tgctgaaggg cgacgacagg cggacggcac aagcccgctt ccccgatttac   480 ggtattcccg acgatttat ctccgtcccc ctgcctgccg gtttgcggag cggaaaagcc     540
cttgtccgca tcaggcagac gggaaaaaac agcggcacaa tcgacaatac cggcggcaca    600
cataccgccg acctctcccg attccccatc accgcgcgca aacagcaat caaaggcagg     660 tttgaaggaa ccgcttcct cccctaccac acgcgcaacc aaatcaacgg cggcgcgctt     720
gacggcaaag ccccgatact cggttacgcc gaagaccctg tcgaactttt ttttatgcac    780
atccaaggct cgggccgtct gaaaaccccg tccggcaaat acatccgcat cggctatgcc    840
gacaaaaacg aacatccyta cgtttccatc ggacgctata tggcggataa gggctacctc    900
aaactcggac aaacctccat gcagggcatt aagtcttata tgcggcaaaa tccgcaacgc    960
ctcgccgaag ttttgggtca aaaccccagc tatatctttt tccgcgagct tgccggaagc   1020
agcaatgacg gccctgtcgg cgcactgggc acgccgctga tgggggaata tgccggcgca   1080
gtcgaccggc actacattac cttgggtgcg cccttatttg tcgccaccgc ccatccggtt   1140
acccgcaaag ccctcaaccg cctgattatg gcgcaggata ccggcagcgc gattaaaggc   1200
gcggtgcgcg tggattattt ttggggatac ggcgacgaag ccggcgaact tgccggcaaa   1260
cagaaaacca cgggatatgt ctggcagctc ctacccaacg gtatgaagcc cgaataccgc   1320
ccgtaa                                                               1326
```

<210> SEQ ID NO 31  
<211> LENGTH: 441  
<212> TYPE: PRT  
<213> ORGANISM: Neisseria meningitidis

<400> SEQUENCE: 31

```
Met Lys Lys Tyr Leu Phe Arg Ala Ala Leu Tyr Gly Ile Ala Ala
1               5                  10                 15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
```

```
              165                 170                 175
Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
            195                 200                 205

Pro Ile Thr Ala Arg Thr Thr Ala Ile Lys Gly Arg Phe Glu Gly Ser
        210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
                260                 265                 270

Lys Tyr Ile Arg Ile Gly Tyr Ala Asp Lys Asn Glu His Pro Tyr Val
            275                 280                 285

Ser Ile Gly Arg Tyr Met Ala Asp Lys Gly Tyr Leu Lys Leu Gly Gln
            290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
                340                 345                 350

Leu Met Gly Glu Tyr Ala Gly Ala Val Asp Arg His Tyr Ile Thr Leu
                355                 360                 365

Gly Ala Pro Leu Phe Val Ala Thr Ala His Pro Val Thr Arg Lys Ala
        370                 375                 380

Leu Asn Arg Leu Ile Met Ala Gln Asp Thr Gly Ser Ala Ile Asp Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
                420                 425                 430

Asn Gly Met Lys Pro Glu Tyr Arg Pro
        435                 440

<210> SEQ ID NO 32
<211> LENGTH: 797
<212> TYPE: PRT
<213> ORGANISM: Neisseria meningitidis

<400> SEQUENCE: 32

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
```

```
                    100                 105                 110
Leu Glu Ser Phe Gly Leu Ala Gln Ser Gln Tyr Phe Asn Gln Ala Thr
            115                 120                 125
Leu Asn Gln Ala Val Ala Gly Leu Lys Glu Glu Tyr Leu Gly Arg Gly
            130                 135                 140
Lys Leu Asn Ile Gln Ile Thr Pro Lys Val Thr Lys Leu Ala Arg Asn
145                 150                 155                 160
Arg Val Asp Ile Asp Ile Thr Ile Asp Glu Gly Lys Ser Ala Lys Ile
                165                 170                 175
Thr Asp Ile Glu Phe Glu Gly Asn Gln Val Tyr Ser Asp Arg Lys Leu
            180                 185                 190
Met Arg Gln Met Ser Leu Thr Glu Gly Gly Ile Trp Thr Trp Leu Thr
            195                 200                 205
Arg Ser Asn Gln Phe Asn Glu Gln Lys Phe Ala Gln Asp Met Glu Lys
210                 215                 220
Val Thr Asp Phe Tyr Gln Asn Asn Gly Tyr Phe Asp Phe Arg Ile Leu
225                 230                 235                 240
Asp Thr Asp Ile Gln Thr Asn Glu Asp Lys Thr Lys Gln Thr Ile Lys
                245                 250                 255
Ile Thr Val His Glu Gly Gly Arg Phe Arg Trp Gly Lys Val Ser Ile
            260                 265                 270
Glu Gly Asp Thr Asn Glu Val Pro Lys Ala Glu Leu Glu Lys Leu Leu
            275                 280                 285
Thr Met Lys Pro Gly Lys Trp Tyr Glu Arg Gln Gln Met Thr Ala Val
            290                 295                 300
Leu Gly Glu Ile Gln Asn Arg Met Gly Ser Ala Gly Tyr Ala Tyr Ser
305                 310                 315                 320
Glu Ile Ser Val Gln Pro Leu Pro Asn Ala Glu Thr Lys Thr Val Asp
                325                 330                 335
Phe Val Leu His Ile Glu Pro Gly Arg Lys Ile Tyr Val Asn Glu Ile
            340                 345                 350
His Ile Thr Gly Asn Asn Lys Thr Arg Asp Glu Val Val Arg Arg Glu
            355                 360                 365
Leu Arg Gln Met Glu Ser Ala Pro Tyr Asp Thr Ser Lys Leu Gln Arg
            370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                405                 410                 415
Ser Leu Thr Glu Arg Ser Thr Gly Ser Leu Asp Leu Ser Ala Gly Trp
            420                 425                 430
Val Gln Asp Thr Gly Leu Val Met Ser Ala Gly Val Ser Gln Asp Asn
            435                 440                 445
Leu Phe Gly Thr Gly Lys Ser Ala Ala Leu Arg Ala Ser Arg Ser Lys
            450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Val Tyr Gly Lys Ala Phe Asp Pro
                485                 490                 495
Arg Lys Ala Ser Thr Ser Ile Lys Gln Tyr Lys Thr Thr Ala Gly
            500                 505                 510
Ala Gly Ile Arg Met Ser Val Pro Val Thr Glu Tyr Asp Arg Val Asn
            515                 520                 525
```

```
Phe Gly Leu Val Ala Glu His Leu Thr Val Asn Thr Tyr Asn Lys Ala
            530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
            595                 600                 605

Tyr Ser Ala Thr His Asn Gln Thr Trp Phe Phe Pro Leu Ser Lys Thr
            610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
            675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
            755                 760                 765

Pro Met Lys Phe Ser Tyr Ala Tyr Pro Leu Lys Lys Lys Pro Glu Asp
            770                 775                 780

Glu Ile Gln Arg Phe Gln Phe Gln Leu Gly Thr Thr Phe
785                 790                 795

<210> SEQ ID NO 33
<211> LENGTH: 792
<212> TYPE: PRT
<213> ORGANISM: Neisseria gonorrhoeae

<400> SEQUENCE: 33

Met Lys Leu Lys Gln Ile Ala Ser Ala Leu Met Met Leu Gly Ile Ser
1               5                   10                  15

Pro Leu Ala Phe Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110
```

-continued

```
Leu Glu Ser Phe Gly Leu Ala Gln Ser Gln Tyr Phe Asn Gln Ala Thr
    115                 120                 125
Leu Asn Gln Ala Val Ala Gly Leu Lys Glu Glu Tyr Leu Gly Arg Gly
    130                 135                 140
Lys Leu Asn Ile Gln Ile Thr Pro Lys Val Thr Lys Leu Ala Arg Asn
145                 150                 155                 160
Arg Val Asp Ile Asp Ile Thr Ile Asp Glu Gly Lys Ser Ala Lys Ile
                    165                 170                 175
Thr Asp Ile Glu Phe Glu Gly Asn Gln Val Tyr Ser Asp Arg Lys Leu
                    180                 185                 190
Met Arg Gln Met Ser Leu Thr Glu Gly Gly Ile Trp Thr Trp Leu Thr
                    195                 200                 205
Arg Ser Asp Arg Phe Asp Arg Gln Lys Phe Ala Gln Asp Met Glu Lys
    210                 215                 220
Val Thr Asp Phe Tyr Gln Asn Asn Gly Tyr Phe Asp Phe Arg Ile Leu
225                 230                 235                 240
Asp Thr Asp Ile Gln Thr Asn Glu Asp Lys Thr Arg Gln Thr Ile Lys
                    245                 250                 255
Ile Thr Val His Glu Gly Gly Arg Phe Arg Trp Gly Lys Val Ser Ile
                    260                 265                 270
Glu Gly Asp Thr Asn Glu Val Pro Lys Ala Glu Leu Glu Lys Leu Leu
                    275                 280                 285
Thr Met Lys Pro Gly Lys Trp Tyr Glu Arg Gln Gln Met Thr Ala Val
    290                 295                 300
Leu Gly Glu Ile Gln Asn Arg Met Gly Ser Ala Gly Tyr Ala Tyr Ser
305                 310                 315                 320
Glu Ile Ser Val Gln Pro Leu Pro Asn Ala Gly Thr Lys Thr Val Asp
                    325                 330                 335
Phe Val Leu His Ile Glu Pro Gly Arg Lys Ile Tyr Val Asn Glu Ile
                    340                 345                 350
His Ile Thr Gly Asn Asn Lys Thr Arg Asp Glu Val Val Arg Arg Glu
                    355                 360                 365
Leu Arg Gln Met Glu Ser Ala Pro Tyr Asp Thr Ser Lys Leu Gln Arg
    370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                    405                 410                 415
Ser Leu Thr Glu Arg Ser Thr Gly Ser Leu Asp Leu Ser Ala Gly Trp
                    420                 425                 430
Val Gln Asp Thr Gly Leu Val Met Ser Ala Gly Val Ser Gln Asp Asn
    435                 440                 445
Leu Phe Gly Thr Gly Lys Ser Ala Ala Leu Arg Ala Ser Arg Ser Lys
    450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Ile Tyr Gly Lys Ala Phe Asp Pro
                    485                 490                 495
Arg Lys Ala Ser Thr Ser Val Lys Gln Tyr Lys Thr Thr Thr Ala Gly
                    500                 505                 510
Gly Gly Val Arg Met Gly Ile Pro Val Thr Glu Tyr Asp Arg Val Asn
                    515                 520                 525
Phe Gly Leu Ala Ala Glu His Leu Thr Val Asn Thr Tyr Asn Lys Ala
    530                 535                 540
```

```
Pro Lys Arg Tyr Ala Asp Phe Ile Arg Lys Tyr Gly Lys Thr Asp Gly
545                 550                 555                 560

Ala Asp Gly Ser Phe Lys Gly Leu Leu Tyr Lys Gly Thr Val Gly Trp
                565                 570                 575

Gly Arg Asn Lys Thr Asp Ser Ala Ser Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Phe Pro Leu Ser Lys Thr
610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Arg Thr Tyr Thr Ala Ala Glu Asn Gly Asn Asn Lys Ser Val Tyr Ser
                725                 730                 735

Glu Asn Ala His Lys Ser Thr Phe Thr Asn Glu Leu Arg Tyr Ser Ala
            740                 745                 750

Gly Gly Ala Val Thr Trp Leu Ser Pro Leu Gly Pro Met Lys Phe Ser
        755                 760                 765

Tyr Ala Tyr Pro Leu Lys Lys Lys Pro Glu Asp Glu Ile Gln Arg Phe
770                 775                 780

Gln Phe Gln Leu Gly Thr Thr Phe
785                 790

<210> SEQ ID NO 34
<211> LENGTH: 797
<212> TYPE: PRT
<213> ORGANISM: Neisseria meningitidis

<400> SEQUENCE: 34

Met Lys Leu Lys Gln Ile Ala Ser Ala Leu Met Val Leu Gly Ile Ser
1               5                   10                  15

Pro Leu Ala Leu Ala Asp Phe Thr Ile Gln Asp Ile Arg Val Glu Gly
                20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
        50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125
```

```
Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
    210                 215                 220

Val Thr Asp Phe Tyr Gln Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
            260                 265                 270

Glu Gly Asp Thr Asn Glu Val Pro Lys Ala Glu Leu Glu Lys Leu Leu
        275                 280                 285

Thr Met Lys Pro Gly Lys Trp Tyr Glu Arg Gln Gln Met Thr Ala Val
    290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
        435                 440                 445

Leu Phe Gly Thr Gly Lys Ser Ala Ala Leu Arg Ala Ser Arg Ser Lys
    450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Ala Gly
            500                 505                 510

Ala Gly Ile Arg Met Ser Val Pro Val Thr Glu Tyr Asp Arg Val Asn
        515                 520                 525

Phe Gly Leu Val Ala Glu His Leu Thr Val Asn Thr Tyr Asn Lys Ala
    530                 535                 540

Pro Lys His Tyr Ala Asp Phe Ile Lys Lys Tyr Gly Lys Thr Asp Gly
```

```
                545                 550                 555                 560

Thr Asp Gly Ser Phe Lys Gly Trp Leu Tyr Lys Gly Thr Val Gly Trp
                            565                 570                 575

Gly Arg Asn Lys Thr Asp Ser Ala Leu Trp Pro Thr Arg Gly Tyr Leu
                        580                 585                 590

Thr Gly Val Asn Ala Glu Ile Ala Leu Pro Gly Ser Lys Leu Gln Tyr
                    595                 600                 605

Tyr Ser Ala Thr His Asn Gln Thr Trp Phe Phe Pro Leu Ser Lys Thr
                610                 615                 620

Phe Thr Leu Met Leu Gly Gly Glu Val Gly Ile Ala Gly Gly Tyr Gly
            625                 630                 635                 640

Arg Thr Lys Glu Ile Pro Phe Phe Glu Asn Phe Tyr Gly Gly Gly Leu
                            645                 650                 655

Gly Ser Val Arg Gly Tyr Glu Ser Gly Thr Leu Gly Pro Lys Val Tyr
                        660                 665                 670

Asp Glu Tyr Gly Glu Lys Ile Ser Tyr Gly Gly Asn Lys Lys Ala Asn
                    675                 680                 685

Val Ser Ala Glu Leu Leu Phe Pro Met Pro Gly Ala Lys Asp Ala Arg
                690                 695                 700

Thr Val Arg Leu Ser Leu Phe Ala Asp Ala Gly Ser Val Trp Asp Gly
            705                 710                 715                 720

Lys Thr Tyr Asp Asp Asn Ser Ser Ser Ala Thr Gly Gly Arg Val Gln
                            725                 730                 735

Asn Ile Tyr Gly Ala Gly Asn Thr His Lys Ser Thr Phe Thr Asn Glu
                        740                 745                 750

Leu Arg Tyr Ser Ala Gly Gly Ala Val Thr Trp Leu Ser Pro Leu Gly
                    755                 760                 765

Pro Met Lys Phe Ser Tyr Ala Tyr Pro Leu Lys Lys Lys Pro Glu Asp
                770                 775                 780

Glu Ile Gln Arg Phe Gln Phe Gln Leu Gly Thr Thr Phe
            785                 790                 795
```

ENHANCEMENT OF BACTERICIDAL ACTIVITY OF NEISSERIA ANTIGENS WITH OLIGONUCLEOTIDES CONTAINING CG MOTIFS

All documents cited herein are hereby incorporated by reference in their entirety.

TECHNICAL FIELD

The present invention is related generally to the field of immune responses and specifically to immunogenic compositions comprising *Neisseria* antigens and oligonucleotides comprising a CG motif for therapeutic and prophylactic administration.

BACKGROUND ART

*Neisseria* are Gram-negative cocci, 0.6 to 1.0 µm in diameter. Two species of *Neisseria* are of major medical importance: *N. gonorrhoeae*, the causative agent of gonorrhoea, and *N. meningitidis*, the causative agent of bacterial meningitis. Humans are the only known reservoir of the members of the genus *Neisseria*. It is well recognized that for a vaccine against *N. meningitidis* or *N. gonorrhoeae* to be efficacious, bactericidal antibodies able to kill the bacterium in the presence of complement must be elicited. Current vaccine formulations against meningococcal B strains, for example, focus on polysaccharides and outer membrane proteins, which are highly variable proteins with little or no cross-reactivity between strains. In addition, there is no current vaccine for gonococcal strains. Accordingly, an improved immunogenic composition for both *Neisseria gonorrhoeae* and *Neisseria meningitidis*, which may be used in vaccine compositions, is highly desired. In addition, an immunogenic composition comprising an adjuvant which is able to elicit an antibactericidal response to *N. meningitidis* and *N. gonorrhoeae* is also highly desired.

Adjuvants are compounds which are capable of potentiating an immune response to antigens. Adjuvants can potentiate both humoral and cellular immunity. For certain pathogens, however, it is preferable to stimulate cellular immunity and, indeed, T cells. Presently used adjuvants do not adequately induce T cell responses, and/or have deleterious side effects.

Currently, the only adjuvants approved for human use in the United States are aluminum salts (alum). These adjuvants have been useful for some vaccines including hepatitis B, diphtheria, polio, rabies, and influenza, but may not be useful for others, especially if stimulation of cell-mediated immunity is required for protection. For example, reports indicate that alum failed to improve the effectiveness of whooping cough and typhoid vaccines and provided only a slight effect with adenovirus vaccines. Additionally, problems such as, induction of granulomas at the injection site and lot-to-lot variation of alum preparations have been experienced.

Complete Freund's adjuvant (CFA) is a powerful immunostimulatory agent that has been used successfully with many antigens on an experimental basis, and especially for animal research. CFA is comprised of three components: a mineral oil, an emulsifying agent such as Arlacel A, and killed mycobacteria such as *Mycobacterium tuberculosis*. Aqueous antigen solutions are mixed with these components to create a water-in-oil emulsion. CFA causes severe side effects, however, including pain, abscess formation, and fever, which prevent its use in either human or veterinary vaccines. The side effects are primarily due to the host's reactions to the mycobacterial component of CFA. Incomplete Freund's adjuvant (IFA) is similar to CFA without the bacterial component. While not yet approved for use in the United States, IFA has been useful for several types of vaccines in other countries. IFA has been used successfully in humans with influenza and polio vaccines and with several animal vaccines including rabies, canine distemper, and foot-and-mouth disease. Experiments have shown, however, that both the oil and emulsifier used in IFA can cause tumors in mice, indicating that an alternative adjuvant would be a better choice for human use.

Muramyl dipeptide (MDP) represents the minimal unit of the mycobacterial cell wall complex that generates the adjuvant activity observed with CFA. Ellouz et al., *Biochem. Biophys. Res. Comm.*, 1974, 59, 1317. Many synthetic analogs of MDP have been generated that exhibit a wide range of adjuvant potency and side effects. Chedid et al., *Prog. Allergy*, 1978, 25, 63. Three analogs of MDP—threonyl derivatives of MDP (Byars et al.; *Vaccine*, 1987, 5, 223); n-butyl derivatives of MDP (Chedid et al., *Infect. Immun.*, 1982, 35, 417); and lipophilic derivatives of muramyl tripeptide (Gisler et al., *Immunomodulations of Microbial Products and Related Synthetic Compounds*, Y. Yamamura and S. Kotani, Eds., Excerpta Medica, Amsterdam, p. 167)—have been shown to stimulate humoral and cell-mediated immunity and exhibit low levels of toxicity. Another derivative of MDP, N-acetylmuramyl-L-alanyl-D-isoglutaminyl-L-alanine-2-[1,2-d] palmitoyl-sn-glycero-3-3(hydroxyphosphoryl-oxy)]ethylamide (MTP-PE) is lipophilic. MTP-PE has phospholipid tails that allow association of the hydrophobic portion of the molecule with a lipid environment while the muramyl peptide portion associates with the aqueous environment. Thus, MTP-PE itself can act as an emulsifying agent to generate stable oil-in-water emulsions.

Levamisole and isoprinosine are other synthetic adjuvants that increase host immunity. Levamisole is the levo isomer of tetramisole and potentiates humoral and cellular immunity through a T cell-dependent mechanism. Isoprinosine, a complex containing inosine, the purine precursor of adenosine and guanosine, promotes T cell mitogenesis. Tuftsin, a 4 amino acid peptide (Thr-Lys-Pro-Arg) homologous to a sequence in the immunoglobulin (Ig) heavy chain, primarily stimulates macrophages.

Microparticles prepared from the biodegradable and biocompatible polymers, known as the poly(lactide-co-glycolides) (PLG), have been demonstrated to be effective adjuvants for a number of antigens. In addition, PLG microparticles can control the rate of release of entrapped antigens and, thus, offer potential for single-dose vaccines. Moreover, administration of biodegradable polymers with entrapped antigens have been demonstrated in a range of animal models to induce potent immune responses. O'Hagan et al., *Advanced Drug Deliv. Rev.*, 1998, 32, 225-246 and Singh et al., *Advanced Drug Deliv. Rev.*, 1998, 34, 285-304.

An emulsion comprising squalene, sorbitan trioleate (Span85™), and polysorbate 80 (Tween 80™) microfluidized to provide uniformly sized microdroplets, i.e. MF59, has also been shown to induce potent immune responses. MF59 formulations have been shown to induce antibody titers 5->100 times greater than those obtained with aluminum salt adjuvants. MF59 has been demonstrated to enhance the immune response to antigens from numerous sources including, for example, herpes simplex virus (HSV), human immunodeficiency virus (HIV), influenza virus, hepatitis C virus (HCV), cytomegalovirus (CMV), hepatitis B virus (HBV), human papillomavirus (HPV), and malaria. Ott et al., *Vaccine Design: The Subunit And Adjuvant Approach*, 1995, M. F. Powell and M. J. Newman, Eds., Plenum Press, New York, p.

277-296; Singh et al., *Vaccine*, 1998, 16, 1822-1827; Ott et al., Vaccine, 1995, 13, 1557-1562; O'Hagan et al., *Mol. Medicine. Today*, 1997, February, 69-75; and Traquina et al., *J. Infect. Dis.*, 1996, 174, 1168-75, the disclosures of which are incorporated herein by reference in their entirety. MF59 adjuvant improves the immunogenicity of subunit antigens while maintaining the safety and tolerability profile of alum adjuvant. Van Nest et al., *Vaccines* 92, 1992, Cold Spring Harbor Laboratory Press, 57-62 and Valensi et al., *J. Immunol.*, 1994, 153, 4029-39, the disclosures of which are incorporated herein by reference in their entirety. MF59 is further described in U.S. patent application Ser. No. 08/434,512, filed May 4, 1995, the disclosure of which is incorporated herein by reference in its entirety. In animal studies, MF59 has not been found to be genotoxic, teratogenic, nor cause sensitization. The mechanism of action of MF59 appears to be dependent upon the generation of a strong CD4+ T cell, i.e., a Th2 cell response. MF59 adjuvants, however, elicit little, if any, Th1 responses, or cytotoxic T lymphocyte (CTL) responses.

Oligonucleotides comprising CpG motifs mixed with antigens have been demonstrated to induce strong Th1 immune responses. Roman et al., *Nat. Med.*, 1997, 3, 849-854; Weiner et al., *Proc. Natl. Acad. Sci. USA*, 1997, 94, 10833-10837; Davis et al., *J. Immunol.*, 1998, 160, 870-876; Chu et al., *J. Exp. Med.*, 1997, 186, 1623-1631; Lipford et al., *Eur. J. Immunol.*, 1997, 27, 2340-2344; and Moldoveanu et al., *Vaccine*, 1988, 16, 1216-1224, the disclosures of which are incorporated herein by reference in their entirety. Unmethylated CpG dinucleotides are relatively common in bacterial DNA, but are underrepresented and methylated in vertebrate DNA. Bird, *Trends Genet.*, 1987, 3, 342-347. Bacterial DNA or synthetic oligonucleotides containing unmethylated CpG motifs are also known to induce immune responses including, for example, B cell proliferation, interleukin-6 and immunoglobulin secretion, and apoptosis resistance. Krieg et al., *Nature*, 1995, 374, 546-549; Klinman et al., *Proc. Natl. Acad. Sci. USA*, 1996, 93, 2879-2883; Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol.*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-5906; PCT publications WO96/02555, WO98/16247, WO98/18810, WO98/40100, WO98/55495, WO98/37919 and WO98/52581, the disclosures of which are incorporated herein by reference in their entirety. CpG oligonucleotides, however, have not been shown to induce bactericidal antibody responses.

An effective immunogenic composition comprising an adjuvant in combination with a *Neisseria* antigen which induces bactericidal antibodies and which can be used for prophylactic and therapeutic treatment in animals for research is highly desired. In addition, an effective immunogenic composition comprising an adjuvant in combination with a *Neisseria* antigen which induces bactericidal antibodies and which can be used for prophylactic and therapeutic treatment in humans is also still desired. Such a response would be helpful in treatment of, for example, meningococcal or gonococcal infections as well as for immunizing individuals susceptible to meningococcal or gonococcal infections.

DISCLOSURE OF THE INVENTION

The present invention is directed to adjuvant compositions comprising an oligonucleotide comprising at least one CG motif, and complete Freund's adjuvant (CFA). Preferably, the oligonucleotide comprises at least one phosphorothioate bond. The oligonucleotide preferably comprises a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, and SEQ ID NO:27. In some embodiments of the invention, the oligonucleotide comprises a CG motif flanked by two purines immediately 5' to the CG motif and two pyrimidines immediately 3' to the CG motif. In preferred embodiments of the invention, the oligonucleotide comprises a nucleotide sequence selected from the group consisting of SEQ ID NO:1, SEQ ID NO:2, SEQ ID NO:3, SEQ ID NO:7, SEQ ID NO:8, SEQ ID NO:9, SEQ ID NO:12, SEQ ID NO:13, SEQ ID NO:19, SEQ ID NO:20, SEQ ID NO:21, SEQ ID NO:22, SEQ ID NO:23, SEQ ID NO:24, and SEQ ID NO:25.

The present invention is also directed to immunogenic compositions comprising an immunostimulating amount of a *Neisseria* antigen, and an immunostimulating amount of an adjuvant composition comprising at least an oligonucleotide comprising at least one CG motif. Preferably, the adjuvant composition comprises at least one oligonucleotide comprising at least one CG motif along with a second adjuvant. Preferably, the *Neisseria* antigen is selected from the group consisting of a protein, protein-polysaccharide, protein-lipopolysaccharide, polysaccharide, and lipopolysaccharide. Preferably, the *Neisseria* antigen is from *Neisseria meningitidis* or *Neisseria gonorrhoeae*. In preferred embodiments of the invention, the *Neisseria* antigen is a *Neisseria meningitidis* group B peptide, preferably comprising SEQ ID NO:31. In some embodiments of the invention, the adjuvant composition comprises a second adjuvant such as, for example, alum, incomplete Freund's adjuvant, or complete Freund's adjuvant. In other embodiments of the invention, the adjuvant composition comprises an oil droplet emulsion as a second adjuvant, which preferably comprises a metabolizable oil and an emulsifying agent. Preferably, the oil and emulsifying agent are present in the form of an oil-in-water emulsion having oil droplets substantially all of which are less than 1 micron in diameter and existing in the absence of any polyoxypropylene-polyoxyethylene block copolymer. Preferably, the oil is an animal oil or vegetable oil, more preferably an unsaturated hydrocarbon, more preferably a terpenoid such as squalene. In preferred embodiments, the composition comprises 0.5 to 20% by volume of oil in an aqueous medium. Preferably, the emulsifying agent comprises a non-ionic detergent. Preferably, the emulsifying agent comprises a polyoxyethylene sorbitan mono-, di-, or triester or a sorbitan mono-, di-, or triether. In some embodiments of the invention, the composition comprises 0.01 to 0.5% by weight of the emulsifying agent.

The compositions of the invention can also comprise a separate immunostimulating agent such as, for example, a bacterial cell wall component and muramyl peptide. In preferred embodiments of the invention, the composition comprises any of the oligonucleotides comprising at least one CG motif described herein.

The present invention is also directed to vaccine compositions comprising an immunostimulating amount of a *Neisseria* antigen, as described herein, and an immunostimulating amount of an adjuvant composition, as described herein, which comprises an oligonucleotide comprising at least one CG motif, as described herein.

The present invention is also directed to methods of stimulating an immune response in a host animal comprising administering to the animal an immunogenic composition described herein in an amount effective to induce an immune response. Preferably, the host animal is a mammal.

The present invention is also directed to methods of immunizing a host animal against Neisseria infection comprising administering to the animal a vaccine composition, as described herein, in an amount effective to induce a protective response. Preferably, the host animal is a mammal, more preferably a human.

The present invention is also directed to methods of immunizing a host animal against *Neisseria meningitidis* comprising administering to the animal a vaccine composition, as described herein, in an amount effective to induce a protective response, wherein the antigen is a *Neisseria meningitidis* group B peptide, preferably comprising. SEQ ID NO:31. Preferably, the host animal is a mammal, more preferably a human.

The practice of the present invention will employ, unless otherwise indicated, conventional methods of virology, immunology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); *DNA Cloning: A Practical Approach*, Vols. I & II (D. Glover, ed.); *Methods In Enzymology* (S. Colowick and N. Kaplan eds., Academic Press, Inc.); *Handbook of Experimental Immunology*, Vols. I-IV (D. M. Weir and C. C. Blackwell eds., Blackwell Scientific Publications); and Fundamental Virology, 2nd Edition, Vols. I & II (B. N. Fields and D. M. Knipe, eds.).

The present invention is directed, in part, to immunogenic compositions comprising a Neisseria antigen, an adjuvant, and an oligonucleotide comprising at least one CG motif. The immunogenic compositions of the invention increased immunogenicity of the antigen almost 10-fold, as judged by antibody titers. Surprisingly, when the sera from immunized animals were tested in a MenB bactericidal assay, a two-fold increase in the capacity of killing MenB cells was observed.

As used herein, the phrase "nucleic acid" refers to DNA, RNA, or chimeras formed therefrom.

As used herein, the phrase "oligonucleotide comprising at least one CG motif" refers to a polynucleotide comprising at least one CG dinucleotide. Oligonucleotides comprising at least one CG motif can comprise multiple CG motifs. These oligonucleotide are also known in the art as "CpG" oligonucleotides in the art. As used herein, the phrase "CG motif" refers to a dinucleotide portion of an oligonucleotide which comprises a cytosine nucleotide followed by a guanosine nucleotide. 5-methylcytosine can also be used in place of cytosine.

As used herein, the phrase "oil droplet emulsion" refers to an emulsion comprising a metabolizable oil and an emulsifying agent.

As used herein, the term "about" means±about 10% of the value it modifies.

As used herein, the phrase "*Neisseria* antigen" means any protein, peptide, protein-polysaccharide, protein-lipopolysaccharide, peptide-polysaccharide, peptide-lipopolysaccharide, polysaccharide, or lipopolysaccharide derived from a *Neisseria* bacterium. Preferably, the *Neisseria* antigen stimulates formation of specific antibodies and reacts specifically in vivo or in vitro with a homologous antibody and/or stimulates a cellular T cell response. The *Neisseria* antigen can be derived from any *Neisseria* species, but is preferably derived from either *N. meningitidis* or *N. gonorrhoeae*. One skilled in the art is readily able to identify and prepare numerous *Neisseria* antigens.

As used herein, the term "vaccine" means an immunogenic composition which is able to induce a microbicidal immune response. Preferably, the vaccines of the present invention elicit a bactericidal antibody response.

According to the present invention, compositions and methods are provided which prophylactically and/or therapeutically immunize or treat a host animal against *Neisseria* infections. The methods of the present invention are useful for conferring prophylactic and therapeutic immunity to a mammal, preferably a human. The methods of the present invention can also be practiced on mammals, other than humans, for biomedical research.

In one embodiment of the present invention, an oligonucleotide comprising at least one CG motif is combined with CFA to form an adjuvant composition, which can be used with any antigen. Oligonucleotides comprising at least one CG motif can be prepared using conventional oligonucleotide synthesis well known to the skilled artisan. Preferably, the oligonucleotides of the invention comprise a modified backbone, such as a phosphorothioate or peptide nucleic acid, so as to confer nuclease resistance to the oligonucleotide. Additional backbones that can be used in the present invention are well known to those skilled in the art. In addition, the oligonucleotide preferably comprises between about 6 and about 100 nucleotides, more preferably between about 8 and about 50 nucleotides, most preferably between about 10 and about 40 nucleotides. In addition, the oligonucleotides of the invention can comprise substitutions of the sugar moieties and nitrogenous base moieties which are well known to those skilled in the art. Preferred oligonucleotides comprising at least one CG motif are disclosed in, for example, Krieg et al., *Proc. Natl. Acad. Sci. USA*, 1998, 95, 12631-12636, Klinman et al., *Proc. Natl. Acad. Sci. USA*, 1996, 93, 2879-2883, Weiner et al., *Proc. Natl. Acad. Sci. USA*, 1997, 94, 10833-10837, Chu et al., *J. Exp. Med.*, 1997, 186, 1623-1631, Brazolot-Millan et al., *Proc. Natl. Acad. Sci. USA*, 1998, 95, 15553-15558, Ballas et al., *J. Immunol.*, 1996, 157, 1840-1845, Cowdery et al., *J. Immunol.*, 1996, 156, 4570-4575, Halpern et al., *Cell. Immunol.*, 1996, 167, 72-78, Yamamoto et al., *Jpn. J. Cancer Res.*, 1988, 79, 866-873, Stacey et al., *J. Immunol.*, 1996, 157, 2116-2122, Messina et al., *J. Immunol.*, 1991, 147, 1759-1764, Yi et al., *J. Immunol.*, 1996, 157, 4918-4925, Yi et al., *J. Immunol.*, 1996, 157, 5394-5402, Yi et al., *J. Immunol.*, 1998, 160, 4755-4761, Roman et al., *Nat. Med.*, 1997, 3, 849-854, Davis et al., *J. Immunol.*, 1998, 160, 870-876, Lipford et al., *Eur. J. Immunol.*, 1997, 27, 2340-2344, Moldoveanu et al., *Vaccine*, 1988, 16, 1216-1224, Yi et al., *J. Immunol.*, 1998, 160, 5898-5906, PCT publications WO96/02555, WO 98/16247, WO98/18810, WO98/40100, WO98/55495, WO98/37919, WO98/52581, the disclosures of which are incorporated herein by reference in their entirety. It is to be understood that the oligonucleotides of the invention comprise at least one CG motif but can contain a plurality of CG motifs.

Preferred oligonucleotides comprise nucleotide sequences such as, for example, tccatgacgttcctgacgtt (SEQ ID NO:1), ataatcgacgttcaagcaag (SEQ ID NO:2), ggggtcaacgttgaggggg (SEQ ID NO:3), tctcccagcgtgcgccat (SEQ ID NO:4), gagaacgctcgaccttcgat (SEQ ID NO:5), tccatgtcgttcctgatgct (SEQ ID NO:6), tccatgacgttcctgatgct (SEQ ID NO:7), gctagacgttagcgt (SEQ ID NO:8), atcgactctcgagcgttctc (SEQ ID NO:9), gaaccttccatgctgttccg (SEQ ID NO:10), gctagatgttagcgt (SEQ ID NO:11), tcaacgtt (SEQ ID NO:12), gcaacgtt (SEQ ID NO:13), tcgacgtc (SEQ ID NO:14), tcagcgct (SEQ ID NO:15), tcaacgct (SEQ ID NO:16), tcatcgat (SEQ ID NO:17), tcttcgaa (SEQ ID NO:18), tgactgtgaacgttcgagatga (SEQ ID NO:19), tgactgtgaacgttagcgatga (SEQ ID NO:20), tgactgtgaacgttagagcgga (SEQ ID NO:21), gtttgcgcaacgttgt-tgccat (SEQ ID NO:22), atggcaacaacgttgcgcaaac (SEQ ID NO:23), cattggaaaacgttcttcgggg (SEQ ID NO:24), ccccgaa-gaacgttttccaatg (SEQ ID NO:25), attgacgtcaat (SEQ ID NO:26), and ctttccattgacgtcaatgggt (SEQ ID NO:27). In preferred embodiments of the invention, the oligonucleotide comprises a CG motif flanked by two purines at the 5' side of the motif and two pyrimidines at the 3' side of the motif. It is to be understood, however, that any oligonucleotide comprising a CG motif can be used in the present invention as long as the oligonucleotide induces an increased immune response.

The present invention is also directed to immunogenic compositions comprising at least one CG oligonucleotide, as described above, and an adjuvant in combination with at least one *Neisseria* antigen. In some embodiments of the invention, the adjuvant is alum, incomplete Freund's adjuvant, or complete Freund's adjuvant. In other embodiments of the invention, the adjuvant comprises an immunogenic amount of an oil droplet emulsion. The adjuvant compositions are generally prepared from the ingredients described below prior to combining the adjuvant with the antigen that will be used in the immunogenic composition.

In some embodiments of the invention, the antigen is derived from *Neisseria gonorrhoeae*. In other embodiments of the invention, the antigen is derived from *Neisseria meningitidis*. Preferably, the antigen is a *Neisseria meningitidis* group B peptide. Preferably, the nucleotide and amino acid sequences of the peptide comprise (SEQ ID NO:30) and (SEQ ID NO:31), respectively. Any *Neisseria* antigen, however, can be used in the present invention. Additional *Neisseria* antigens are described below in the Examples. In addition, peptides which can serve as *Neisseria* antigens of the invention are disclosed in copending application Ser. Nos. 60/083,758, 60/094,689, 60/098,994, 60/103,749, 60/103,794, 60/099,062, 60/121,528 and 60/103,796, and in WO99/24578, WO99/36544 and WO99/57280, the disclosures of which are incorporated herein by reference in their entirety. It is to be understood, single or multiple conservative amino acid substitutions can be made with altering the immunogenicity of the antigens of the invention. In addition, variations in bacterial strains are also encompassed within the nucleotide and amino acid sequences disclosed herein. For example, some strains can comprise Y rather than C at amino acid position 11, A rather than D at position 48, A rather than G at position 55, Q rather than R at position 207, A rather than S at position 312, T rather than A at position 338, and G rather than S at position 341.

Antigen can be added to the adjuvant compositions after preparation. The antigen and emulsion can be mixed by shaking. When using CFA and IFA, antigen in PBS can be mixed with an equal volume of either CFA or IFA. The mixture can be emulsified by passing through a hypodermic needle until a thick, emulsion is achieved.

In preferred embodiments of the invention, an immunostimulating amount of at least one oligonucleotide comprising at least one CG motif and at least one *Neisseria* antigen is combined with an adjuvant comprising an oil droplet emulsion. The oil droplet emulsion preferably comprises a metabolizable oil and an emulsifying agent, wherein the oil and the emulsifying agent are present in the form of an oil-in-water emulsion having oil droplets substantially all of which are less than one micron in diameter. Such droplets show a surprising superiority over adjuvant compositions containing oil and emulsifying agents in which the oil droplets are significantly larger than those provided by the present invention.

The individual components of the present invention, although described below both generally and in some detail for preferred embodiments, are well known in the art, and the terms used herein, such as metabolizable oil, emulsifying agent, immunostimulating agent, muramyl peptide, and lipophilic muramyl peptide, are sufficiently well known to describe these compounds to one skilled in the art without further description.

One component of these compositions is a metabolizable, non-toxic oil, preferably one of 6 to 30 carbon atoms including, but not limited to, alkanes, alkenes, alkynes, and their corresponding acids and alcohols, the ethers and esters thereof, and mixtures thereof. The oil can be any vegetable oil, fish oil, animal oil or synthetically prepared oil which can be metabolized by the body of the host animal to which the immunogenic composition will be administered and which is not toxic to the subject. The host animal is typically a mammal, and preferably a human. Mineral oil and similar toxic petroleum distillate oils are expressly excluded from this invention.

The oil component of this invention can also be any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols can be acylated employing amino- or poly-functional acid, for example acetic acid, propanoic acid, citric acid or the like. Ethers derived from long chain alcohols which are oils and meet the other criteria set forth herein can also be used.

The individual alkane, alkene or alkyne moiety and its acid or alcohol derivatives will generally have about 6 to about 30 carbon atoms. The moiety can have a straight or branched chain structure. It can be fully saturated or have one or more double or triple bonds. Where mono or poly ester- or ether-based oils are employed, the limitation of about 6 to about 30 carbons applies to the individual fatty acid or fatty alcohol moieties, not the total carbon count.

Any metabolizable oil, particularly from an animal, fish or vegetable source, can be used herein. It is essential that the oil be metabolized by the host to which it is administered, otherwise the oil component can cause abscesses, granulomas or even carcinomas, or (when used in veterinary practice) can make the meat of vaccinated birds and animals unacceptable for human consumption due to the deleterious effect the unmetabolized oil can have on the consumer.

Exemplary sources for vegetable oils include nuts, seeds and grains. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like can also be used.

The technology for obtaining vegetable oils is well developed and well known. The compositions of these and other similar oils can be found in, for example, the Merck Index, and source materials on foods, nutrition and food technology.

The 6-10 carbon fatty acid esters of glycerol and 1,2-propanediol, while not occurring naturally in seed oils, can be prepared by hydrolysis, separation and esterification of the appropriate materials starting from the nut and seed oils. These products are commercially available under the name NEOBEE® from PVO International, Inc., Chemical Specialties Division, 416 Division Street, Boongon, N.J., and others.

Oils from any animal source can also be employed in the immunogenic compositions of this invention. Animal oils and fats are usually solids at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and can therefore be used in the practice of this invention. The procedures for separation, purification, saponification and other means necessary for obtaining pure oils from animal sources are well known in the art.

Most fish contain metabolizable oils which can be readily recovered. For example, cod liver oil, shark liver oils, and whale oil such as spermaceti exemplify several of the fish oils which can be used herein. A number of branched chain oils are synthesized biochemically in 5-carbon isoprene units and are generally referred to as terpenoids. Shark liver oil contains a branched, unsaturated terpenoid known as squalene, 2,6,10, 15,19,23-hexamethyl-2,6,10,14,18,22-tetracosahexaene which is particularly preferred herein. Squalane, the saturated analog to squalene, is also a particularly preferred oil. Fish oils, including squalene and squalene, are readily available from commercial sources or can be obtained by methods known in the art.

The oil component of these immunogenic compositions will be present in an amount from about 0.5% to about 20% by volume but preferably no more than about 15%, especially in an amount of about 1% to about 12%. It is most preferred to use from about 1% to about 4% oil.

The aqueous portion of these immunogenic compositions is preferably buffered saline or, more preferably, unadulterated water. Because these compositions are intended for parenteral administration, it is preferable to make up final buffered solutions used as immunogenic compositions so that the tonicity, i.e., osmolality, is essentially the same as normal physiological fluids in order to prevent post-administration swelling or rapid absorption of the composition because of differential ion concentrations between the composition and physiological fluids. It is also preferable to buffer the saline in order to maintain pH compatible with normal physiological conditions. Also, in certain instances, it can be necessary to maintain the pH at a particular level in order to ensure the stability of certain composition components such as the glycopeptides.

Any physiologically acceptable buffer can be used herein, but phosphate buffers are preferred. Other acceptable buffers such acetate, tris, bicarbonate, carbonate, or the like can be used as substitutes for phosphate buffers. The pH of the aqueous component will preferably be between about 6.0-8.0.

When the immunogenic compositions is initially prepared, however, unadulterated water is preferred as the aqueous component of the emulsion. Increasing the salt concentration makes it more difficult to achieve the desired small droplet size. When the final immunogenic compositions is prepared from the oil droplet adjuvant, the antigenic material can be added in a buffer at an appropriate osmolality to provide the desired immunogenic composition.

The quantity of the aqueous component employed in these compositions will be that amount necessary to bring the value of the composition to unity. That is, a quantity of aqueous component sufficient to make 100% will be mixed, with the other components listed above, in order to bring the compositions to volume.

A substantial number of emulsifying and suspending agents are generally used in the pharmaceutical sciences. An emulsifying agent is not a metabolizable oil, as used herein. Emulsifying agents include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long chain fatty-acid-derived compounds form a third substantial group of emulsifying and suspending agents which could be used in this invention. Any of the foregoing surfactants are useful so long as they are non-toxic.

Specific examples of suitable emulsifying agents (also referred to as surfactants or detergents) which can be used in accordance with the present invention include the following:

1. Water-soluble soaps, such as the sodium, potassium, ammonium and alkanol-animonium salts of higher fatty acids ($C_{10}$-$C_{22}$), and, particularly sodium and potassium tallow and coconut soaps.

2. Anionic synthetic non-soap detergents, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid asters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$— sulfonated $C_{10}$-$C_{24}$ α-olefins.

3. Nonionic synthetic detergents made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

4. Nonionic detergents, such as amine oxides, phosphine oxides and sulfoxides, having semipolar characteristics. Specific examples of long chain tertiary amine oxides include dimethyldodecylamine oxide and bis-(2-hydroxyethyl) dodecylamine. Specific examples of phosphine oxides are found in U.S. Pat. No. 3,304,263 which issued Feb. 14, 1967, and include dimethyldodecylphosphine oxide and dimethyl-(2-hydroxydodecyl) phosphine oxide.

5. Long chain sulfoxides, including those corresponding to the formula $R^1$—SO—$R^2$ wherein $R^1$ and $R^2$ are substituted or unsubstituted alkyl radicals, the former containing from about 10 to about 28 carbon atoms, whereas $R^2$ contains from 1 to 3 carbon atoms. Specific examples of these sulfoxides include dodecylmethyl sulfoxide and 3-hydroxy tridecyl methyl sulfoxide.

6. Ampholytic synthetic detergents, such as sodium 3-dodecylamino-propionate and sodium 3-dodecylaminopropane sulfonate.

7. Zwitterionic synthetic detergents, such as 3-(N,N-dimethyl-N-hexadecylammonio) propane-1-sulfonate and 3-(N,N-dimethyl-N-hexadecylammonio)-2hydroxy propane-1-sulfonate.

Additionally, all of the following types of emulsifying agents can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight chain hydrophobic groups, as wall as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this paragraph overlap with previously described surfactant classes.

There are a number emulsifying agents specifically designed for and commonly used in biological situations. For example, a number of biological detergents (surfactants) are listed as such by Sigma Chemical Company on page 310-316 of its 1987 Catalog of Biochemical and Organic Compounds. Such surfactants are divided into four basic types: anionic, cationic, zwitterionic, and nonionic. Examples of anionic detergents include alginic acid, caprylic acid, cholic acid, 1-decanesulfonic acid, deoxycholic acid, 1-dodecanesulfonic acid, N-lauroylsarcosine, and taurocholic acid. Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate. Examples of zwitterionic detergents include 3-[(3-cholamidopropyl)-dimethylammonio]-1-propanesulfonate (commonly abbreviated CHAPS), 3-[(cholamidopropyl)-dimethylammonio]-2-hydroxy-1-propanesulfonate (generally abbreviated CHAPSO) N-dodecyl-N,N-dimethyl-3-ammonio-1-propanesulfonate, and lyso-α-phosphatidylcholine. Examples of nonionic detergents include decanoyl-N-methylglucamide, diethylene glycol monopentyl ether, n-dodecyl β-D-glucopyranoside, ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid ethers (e.g., sold under the trade name Tween), and sorbitan fatty acid ethers (e.g., sold under the trade name Span).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid substituted moiety can be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,g-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name SPAN® or ARLACEL®, usually with a letter or number designation which distinguishes between the various mono-, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available from, for example, ICI America's Inc., Wilmington, Del. under the registered mark ATLAS®.

A related group of surfactants comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble oil dispersible in water and soluble to varying degrees in organic liquids.

These materials, commercially available under the mark TWEEN® are useful for preparing oil-in-water emulsions and dispersions or for the solubilization of oils and making anhydrous ointments water-soluble or washable. The TWEEN® surfactants can be combined with a related sorbitan monoester or triester surfactants to promote emulsion stability. TWEEN® surfactants generally have a HLB value falling between 9.6 to 16.7.

A third group of non ionic surfactants which could be used alone or in combination with SPAN®, ARLACEL®, and TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water like TWEEN® surfactants. The MYRJ® surfactants can be blended with TWEEN® surfactants, or with TWEEN®/SPAN® or ARLACEL® surfactant mixtures for use in forming emulsions. MYRJ® surfactants can be made by methods known in the art or are available commercially from ICI America's Inc.

A fourth group of polyoxyethylene based nonionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants can be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which could potentially be used in the practice of this invention are for example: polyoxyethylene, polyol fatty acid esters, polyoxyethylene ether, polyoxypropylene fatty ethers, bee's wax derivatives containing polyoxyethylene, polyoxyethylene lanolin derivative, polyoxyethylen fatty glyceride, glycerol fatty acid esters or other polyoxyethylene acid alcohol or ether derivatives of long-chain fatty acids of 12-22 carbon atoms.

As the immunogenic compositions of this invention are intended to be multi-phase systems, it is preferable to choose an emulsion-forming non-ionic surfactant which has an HLB value in the range of about 7 to 16. This value can be obtained through the use of a single non-ionic surfactant such as a TWEEN® surfactant or can be achieved by the use of a blend of surfactants such as with a sorbitan mono, di- or triester based surfactant; a sorbitan ester polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use a single nonionic surfactant, most particularly a TWEEN® surfactant, as the emulsion stabilizing non-ionic surfactant in the practice of this invention. The surfactant named TWEEN® 80, otherwise known as polysorbate 80 for polyoxyethlyene 20 sorbitan monooleate, is the most preferred of the foregoing surfactants.

Sufficient droplet size reduction can usually be effected by having the surfactant present in an amount of 0.02% to 2.5% by weight (w/w). An amount of 0.05% to 1% is preferred with 0.01 to 0.5% being especially preferred.

The manner in which the droplet size of the invention is reached is not important to the practice of the present invention. One manner in which submicron oil droplets can be obtained is by use of a commercial emulsifiers, such as model number 110Y available from Microfluidics, Newton, Mass. Examples of other commercial emulsifiers include Gaulin Model 30CD (Gaulin, Inc., Everett, Mass.) and Rainnie Minilab Type 8.30H (Miro Atomizer Food and Dairy, Inc., Hudson, Wis.). These emulsifiers operated by the principle of high shear forces developed by forcing fluids through small apertures under high pressure. When the model 110Y is operated at 5,000-30,000 psi, oil droplets having diameters of 100-750 nm are provided.

The size of the oil droplets can be varied by changing the ratio of detergent to oil (increasing the ratio decreases droplet size, operating pressure (increasing operating pressure reduces droplet size), temperature (increasing temperature decreases droplet size), and adding an amphipathic immunostimulating agent (adding such agents decreases droplet size). Actual droplet size will vary with the particular detergent, oil, and immunostimulating agent (if any) and with the particular operating conditions selected. Droplet size can be verified by use of sizing instruments, such as the commercial Sub-Micron Particle Analyzer (Model N4MD) manufactured by the Coulter Corporation, and the parameters can be varied using the guidelines set forth above until substantially all droplets are less than 1 micron in diameter, preferably less than 0.8 microns in diameter, and most preferably less than 0.5 microns in diameter. By substantially all is meant at least about 80% (by number), preferably at least about 90%, more preferably at least about 95%, and most preferably at least about 98%. The particle size distribution is typically Gaussian, so that the average diameter is smaller than the stated limits.

The present invention is practiced by preparing an oil emulsion in the absence of other components previously taught in the prior art to be used with submicron emulsions for satisfactory immunogenicity, namely polyoxylropylene-polyoxyethlyne block polymers such as those described for use with adjuvants in U.S. Pat. Nos. 4,772,466 and 4,770,874 and in EP-A2-0315153.

An immunogenic composition of the invention comprises a metabolizable oil-in-water and an emulsifying agent other than a POP-POE copolymer. The emulsifying agent need not have any specific immunostimulating activity, since the oil composition by itself can function as an adjuvant when the oil droplets are in the sub-micron range. However, increased immunostimulating activity can be provided by including any of the known immunostimulating agents in the composition. These immunostimulating agents can either be separate from the emulsifying agent and the oil or the immunostimulating agent and the emulsifying agent can be one and the same molecule. Examples of the former situation include metabolizable oils mixed with killed mycobacteria, such as *Mycobacterium tuberculosis*, and subcellular components thereof. Additional immunostimulating substances include the muramyl peptides that are components of the cell walls of such bacteria, and include derivatives thereof. Examples of the joint emulsifying agent/immunostimulating agent are the lipophilic muramyl peptides described in Sanchez-Pescador et al., J. Immunol., 1988, 141, 1720-1727, the disclosure of which is incorporated herein by reference in its entirety. These materials comprise the basic N-acetylmuramyl peptide (a hydrophilic moiety) that acts is an immunostimulating group, but also include a lipophilic moiety that provides surface-active characteristics to the resulting compound. Such compounds, as well as other types of amphipathic immunostimulating substances, act as both immunostimulating agents and emulsifying agents and are preferred in the practice of the present invention. In addition, it is also possible to practice the present invention by using a amphipathic immunostimulating substance in combination with a second immunostimulating substance that is not amphipathic. An example would be use of a lipophilic muramyl peptide in combination with an essentially unsubstituted (i.e., essentially hydrophilic) muramyl dipeptide.

A preferred oil droplet emulsion is MF59. MF59 can be made according to the procedures described in, for example, Ott et al., *Vaccine Design: The Subunit And Adjuvant Approach,* 1995, M. F. Powell and M. J. Newman, Eds., Plenum Press, New York, p. 277-296; Singh et al., *Vaccine,* 1998, 16, 1822-1827; Ott et al., *Vaccine,* 1995, 13, 1557-1562; and Valensi et al., *J. Immunol.,* 1994, 153, 4029-39, the disclosures of which are incorporated herein by reference in their entirety.

Animals can be injected with the various adjuvant/immunogenic compositions by intraperitoneal, intramuscular, or subcutaneous routes.

The compositions of an immunogenic composition of the invention will employ an effective amount of an antigen. That is, there will be included an amount of antigen which, in combination with the adjuvant, will cause the subject to produce a specific and sufficient immunological response, preferably a T lymphocyte response, so as to impart protection to the subject from the subsequent exposure to *Neisseria.*

No single dose designation can be assigned which will provide specific guidance for each and every antigen which can be employed in this invention. The effective amount of antigen will be a function of its inherent activity and purity and is empirically determined by those of ordinary skill in the art via routine experimentation. It is contemplated that the adjuvant compositions of this invention can be used in conjunction with whole cell or viral immunogenic compositions as well as with purified antigens or protein subunit or peptide immunogenic compositions prepared by recombinant DNA techniques or synthesis. Since the adjuvant compositions of the invention are stable, the antigen and emulsion can mixed by simple shaking. Other techniques, such as passing a mixture of the adjuvant and solution or suspension of the antigen rapidly through a small opening (such as a hypodermic needle) readily provides a useful immunogenic composition.

The adjuvant and immunogenic compositions according to the present invention comprise about 1 nanogram to about 1000 micrograms of nucleic acid, preferably DNA such as, for example, CG oligonucleotides. In some preferred embodiments, the immunogenic compositions contain about 10 nanograms to about 800 micrograms of nucleic acid. In some preferred embodiments, the immunogenic compositions contain about 0.1 to about 500 micrograms of nucleic acid. In some preferred embodiments, the immunogenic compositions contain about 1 to about 350 micrograms of nucleic acid. In some preferred embodiments, the immunogenic compositions contain about 25 to about 250 micrograms of nucleic acid. In some preferred embodiments, the immunogenic compositions contain about 100 micrograms nucleic acid. One skilled in the art can readily formulate an immunogenic composition comprising any desired amount of nucleic acid. The immunogenic compositions according to the present invention are provided sterile and pyrogen free. The immunogenic compositions can be conveniently administered in unit dosage form and can be prepared by any of the methods well known in the pharmaceutical art, for example, as described in Remington's Pharmaceutical Sciences (Mack Pub. Co., Easton, Pa., 1980), the disclosure of which is incorporated herein by reference in its entirety.

The immunogenic compositions according to the present invention comprise an immunostimulatory amount of *Neisseria* antigen. An immunostimulatory amount is that amount which is sufficient to induce a measurable humoral or cellular immune response. For example, the immunogenic compositions of the present invention comprise about 1 nanogram to about 1000 micrograms of antigen or about 10 nanograms to about 800 micrograms of antigen. In some preferred embodiments, the immunogenic compositions contain about 0.1 to about 500 micrograms of antigen. In some preferred embodiments, the immunogenic compositions contain about 1 to about 350 micrograms of antigen. In some preferred embodiments, the immunogenic compositions contain about 25 to about 250 micrograms of antigen. In some preferred embodiments, the immunogenic compositions contain about 100 micrograms of antigen. One skilled in the art can readily formulate an immunogenic composition comprising any desired amount of antigen, which can be empirically determined by those of ordinary skill in the art via routine experimentation. The immunogenic compositions can be conveniently administered in unit dosage form and can be prepared by any of the methods well known in the pharmaceutical art, for example, as described in Remington's Pharmaceutical Sciences (Mack Pub. Co., Easton, Pa., 1980), the disclosure of which is incorporated herein by reference in its entirety.

The present invention is also direct to a vaccine composition comprising an adjuvant, as described herein, with a CG oligonucleotide, as described herein, in combination with a *Neisseria* antigen, as described herein. Such vaccine compositions, such as the vaccine composition shown in the Examples, elicit a humoral immune response which is bactericidal.

The present invention is also directed to methods of stimulating an immune response in a host animal comprising administering to the animal an immunogenic composition described above in an amount effective to induce an immune response. The host animal is preferably a mammal, more preferably a human. Preferred routes of administration include, but are not limited to, intramuscular, intraperitoneal, intradermal, subcutaneous, intravenous, intraarterially, intraoccularly and oral as well as transdermally or by inhalation or suppository. Most preferred routes of administration include intramuscular, intraperitoneal, intradermal and subcutaneous injection. According to some embodiments of the present invention, the immunogenic composition is administered to a host animal using a needleless injection device, which are well known and widely available. One having ordinary skill in the art can, following the teachings herein, use needleless injection devices to deliver immunogenic compositions to cells of an individual.

The present invention is also directed to methods of immunizing a host animal against or treating a host animal with a *Neisseria* infection comprising administering to the animal an immunogenic or vaccine composition described herein in an amount effective to induce a protective response. The host animal is preferably a mammal, more preferably a human. Preferred routes of administration are, described herein.

MODES FOR CARRYING OUT THE INVENTION

The invention is further illustrated by way of the following examples which are intended to elucidate the invention. The foregoing examples are meant to illustrate the invention and are not to be construed to limit the invention in any way. Those skilled in the art will recognize modifications that are within the spirit and scope of the invention.

Example 1

Preparation of Adjuvant Compositions

MTP-PE was provided by CIBA-GEIGY (Basel, Switzerland). Squalene and TWEEN® 80 were obtained from Sigma Chemical Co. (St. Louis, Mo.). CFA and IFA were obtained from Gibco (Grand Island, N.Y.). Aluminum hydroxide (Rehsorptar) was obtained from Reheis Chemical Co. (Berkeley Heights N.J.).

Preparation of oil droplet emulsions was made by a number of methods. In the first method, a mixture consisting of 4% squalene, 0.008% TWEEN® 80, 250 µg/ml MTP-PE and antigen in phosphate buffered saline (PBS) was passed through a 23 gauge needle 6 times. This emulsion consisted of oil droplet sizes in the range of 10 microns and is termed MTP-PE-LO. The second method comprises passing the above-described mixture through a Kirkland emulsifier five times. This emulsion consists of oil droplets primarily of 1-2 microns and is termed MTP-PE-LO-KE. The Kirkland emulsifier (Kirkland Products, Walnut Creek, Calif.) is a small-scale version of the commercial knife-edged homogenizer (e.g., Gaulin Model 30CD and Rainnie Minilab Type 8.301-1) generating about 1000 psi in the working chamber. In the third method, mixtures containing 0.3-18% squalene and 0.2-1.0 mg/ml MTP-PE with or without TWEEN®80 were passed through the Microfluidizer (Model No. 110Y Microfluidics, Newton, Mass.) at 5,000-30,000 psi. Typically, 50 ml of emulsion was mixed for 5 minutes or 100 ml for 10 minutes in the microfluidizer. The resulting emulsions consisted of oil droplets of 100-750 nm depending on squalene, MTP-PE, and detergent concentration and microfluidizer operating pressure and temperature. This compositions is termed MTP-PE-LO-MF.

Example 2

Antigen Preparation

The gene encoding the MenB antigen 919 was amplified from the MenB chromosomal DNA using the following primers: forward primer 5'-cgcggatcccatatgtgccaaagcaagagcatc-3' (SEQ ID NO:28), reverse primer 5'-cccgctcgagcgggcggtat-tcggg-3' (SEQ ID NO:29).

After amplification, the PCR product was eluted out of an agarose gel and 1 µg of DNA was digested with the restriction enzymes Nde1 and Xho1 which cut at the 5' end and at the 3' end of the amplified fragment, respectively. After digestion, the fragment was purified using the QIAquick Purification Kit (Qiagen) and ligated to plasmid pET (Novagen) previously cut with Nde1 and Xho1. The ligation mixture was used to transform *E. coli* DH5 cells and colonies carrying recombinant plasmids were selected on ampicillin containing plates. From one positive clone, the plasmid, named pET-919, was prepared using the plasmid preparation kit from Qiagen and the plasmid used to transform *E. coli* BL21-DE3 cells.

*E. coli* BL21-DE3 (pGEX-919) strain was grown at 30° C. in 500 ml LB supplemented with 100 µg of Ampicillin. When an $OD_{600}$ value of 0.5 was reached, the culture was supplemented with 1 mM IPTG and cultured for an additional 3 hours. The cells were collected by centrifugation and disrupted in 7.5 ml ice-cold imidazole buffer (300 mM NaCl, 50 mM phosphate buffer, 10 mM imidazole, pH 8) by sonication on ice using a Branson sonifier B-15. After separation of the cellular debris by centrifugation, the supernatant was mixed with 1 ml $Ni^{2+}$-resin (Pharmacia) and kept at room temperature for 30 minutes. The resin was collected by centrifugation, washed with 10 ml ice-cold 10 mM imidazole buffer and loaded on a small disposable column. The column was then washed with 10 ml 20 mM imidazole buffer and finally the protein was eluted with 250 mM imidazole buffer. The protein was dialyzed in PBS and stored at −20° C.

The nucleotide sequence (SEQ ID NO:30) of MenB 919 is shown below:

```
atgaaaaaatacctattccgcgccgccctgtacggcatcgccgccgccat
cctcgccgcctgccaaagcaagagcatccaaaccttccgcaacccgaca
cacccgtcatcaacggcccggaccggccggtcggcatccccgaccccgcc
ggaacgacggtcggcggcggcggggccgtctataccgttgtaccgcacct
gtccctgcccactgggcggcgcaggatttcgccaaaagcctgcaatcct
tccgcctcggctgcgccaatttgaaaaaccgccaaggctggcaggatgcg
tgcgcccaagcctttcaaaccccgtccattcctttcaggcaaaacagtt
ttttgaacgctatttcacgccgtggcaggttgcaggcaacggaagccttg
ccggtacggttaccggctattacgaaccggtgctgaagggcgacgacagg
cggacggcacaagcccgcttcccgatttacggtattcccgacgattttat
ctccgtcccctgcctgccggtttgcggagcggaaaagcccttgtccgca
tcaggcagacgggaaaaaacagcggcacaatcgacaataccggcggcaca
cataccgccgacctctcccgattccccatcaccgcgcgcacaacagcaat
caaaggcaggtttgaaggaagccgcttcctcccctaccacacgcgcaacc
aaatcaacggcggcgcgcttgacggcaaagccccgatactcggttacgcc
gaagaccctgtcgaactttttttttatgcacatccaaggctcgggccgtct
gaaaacccgtccggcaaatacatccgcatcggctatgccgacaaaaacg
aacatccytacgtttccatcggacgctatatggcggataagggctacctc
aaactcggacaaacctccatgcagggcattaagtcttatatgcgcaaaa
tccgcaacgcctcgccgaagtttgggtcaaaacccagctatatctttt
tccgcgagcttgccggaagcagcaatgacggccctgtcggcgcactgggc
acgccgctgatgggggaatatgccggcgcagtcgaccggcactacattac
cttgggtgcgcccttatttgtcgccaccgccatccggttacccgcaaag
ccctcaaccgcctgattatggcgcaggataccggcagcgcgattaaggc
gcggtgcgcgtggattattttggggatacggcgacgaagccggcgaact
tgccggcaaacagaaaaccacgggatatgtctggcagctcctacccaacg
gtatgaagcccgaataccgcccgtaa
```

It is to be understood that "y" is either a "c" or "t".

The amino acid sequence (SEQ ID NO:31) of the MenB 919 peptide is shown below:

```
MKKYLFRAALYGIAAAILAACQSKSIQTFPQPDTSVINGPDRPVGIPDPA
GTTVGGGGAVYTVVPHLSLPHWAAQDFAKSLQSFRLGCANLKNRQGWQDV
CAQAFQTPVHSFQAKQFFERYFTPWQVAGNGSLAGTVTGYYEPVLKGDDR
RTAQARFPIYGIPDDFISVPLPAGLRSGKALVRIRQTGKNSGTIDNTGGT
HTADLSRFPITARTTAIKGRFEGSRFLPYHTRNQINGGALDGKAPILGYA
EDPVELFFMHIQGSGRLKTPSGKYIRIGYADKNEHPYVSIGRYMADKGYL
KLGQTSMQGIKSYMRQNPQRLAEVLGQNPSYIFFRELAGSSNDGPVGALG
TPLMGEYAGAVDRHYITLGAPLFVATAHPVTRKALNRLIMAQDTGSAIDG
AVRVDYFWGYGDEAGELAGKQKTTGYVWQL LPNGMKPEYRP.
```

Example 3

Immunization

Groups of 4 CD1 mice were given one of 5 vaccine formulations (shown below in Table 1).

The vaccines were formulated by mixing 75 µl of protein preparation (20 µg of protein) with 75 µl of the specific adjuvant. When alum was used, 150 µl of a solution containing 20 µg of protein and alum at a final concentration of 1 mg/ml were used. Finally, in the case of 919-CpG oligo-CFA formulation, 20 µg of the phosphorothioate oligodeoxynucleotide (Oligos, Etcd. USA) having the sequence: 5'-tccatgacgt-tcctgacgtt-3' (SEQ ID NO:1) were mixed with 20 µg of protein in a final volume of 75 µl of CFA before immunization. The vaccines were administered i.p. at day 1 and day 21 and serum samples were taken 15 days after each injection.

Example 4

ELISA Assay

MenB M7 cells were collected by centrifugation from a 7 ml liquid culture having an $OD_{620}$ value of 0.4. The cells were washed once in PBS and then resuspended in PBS containing 0.025% formaldehyde. After 2 hour incubation at room temperature and further incubation at 4° C. overnight, the cells were dispensed in 96 well Greiner plates (100 µl/well) and kept overnight at 4° C. The wells were then washed three times with PBT (0.1% Tween-20 in PBS) before adding 200 µl of saturation buffer (2.7% polyvinylpyrrolidone 10 in water). After washing with PBT, 200 µl of diluted sera (dilution buffer: 1% BSA, 0.1% Tween-20, 0.1% $NaN_3$ in PBS) were added to each well and the plates incubated for 90 minutes at 37° C. After washing, 100 µl of HRP-conjugated rabbit anti-mouse (Dako) serum diluted 1:2000 in dilution buffer were added to each well and the plates were incubated for 90 minutes at 37° C. Wells were washed three times with PBT buffer, 100 µl of substrate buffer for HRP (25 ml citrate buffer pH 5.0, 10 mg O-phenyldiamine, 10 µl $H_2O_2$) were added to each well and the plates were kept at room temperature for 20 minutes. Finally, 100 µl $H_2SO_2$ were added to each well and $OD_{490}$ values were taken. ELISA titers were determined arbitrarily as the dilution of serum which gave an O.D. of 0.4. The ELISA titers of the pool of sera from each immunization schedule are reported below in Table 1. As shown, the highest antibody titers after 1 dose of vaccine were 919-IFA and 919-CFA-oligo, the latter giving titers twice as high as 919-IFA. In addition, 919-CFA-oligo resulted in a greater response than the response with and 919-CFA alone. Since antibody titer is being measured, the response is expected to be greater than 919-oligo alone as well. After the second dose, 919-CFA-oligo turned out to be the best formulation, giving antibody titer almost 1 order of magnitude higher than any other formulation used.

TABLE 1

ELISA titres using 919 antigen with different adjuvant formulations

| Formulation | First Dose | Second Dose |
|---|---|---|
| 919-CFA | 876 | 3300 |
| 919-IFA | 2443 | 5031 |
| 919-alum | 120 | 800 |
| 919-MF59 | 120 | 3064 |
| 919-CFA-CG oligo | 4478 | 22652 |

Example 5

Bactericidal Assay

MenB 2996 strain was grown in liquid culture (Muller-Hinton broth) until an $OD_{620}$ value of 0.5-0.8 was reached. Then the cells were collected by centrifugation and resuspended in Gey's buffer 1% BSA (Gibco) obtaining a suspension with an $OD_{620}$ value of 0.5. Finally, the suspension was diluted 1:20,000 in Gey's buffer 1% BSA and stored at 25° C. For bactericidal assay, 50 µl of Gey's buffer containing 1% BSA were added to each well together with 25 µA of diluted mice sera (dilution buffer: Gey's buffer with 1% BSA), 25 µl of bacterial suspension and µl of either heat-inactivated (56° C. for 30 minutes) or normal baby rabbit complement. Immediately after the addition of the baby rabbit complement, 22 µl of each sample were plate on the Muller-Hinton agar plates and then the 96-well plates were incubated at 37° C. under rotation. Samples of 22 µl from each well were plated as before after 1 our incubation. The growth rate of MenB approximately doubles in two hours.

The bactericidal activity of the pools of sera from each group are given in Table 2. The plates were kept at 37° C. until the colonies became visible. The number of MenB bacterial colonies were counted at Time 0 and one hour later. The best bactericidal activity was found in the sera from mice immunized with 919-CFA-oligo formulation, which gave a bactericidal activity at least 2 times higher than other formulations used including 919-CFA. In addition, 919-CFA-oligo resulted in a greater response than the response with and 919-CFA alone. As antibody titer is being measured, the response is expected to be greater than 919-oligo alone as well.

TABLE 2

Bactericidal activity of 919 antigen using different adjuvant formulations

| Formulation | Pre-immune or immune | Sera dilution | Time 0 min | Time 60 min | % survival of MenB |
|---|---|---|---|---|---|
| 919-CFA | Pre-Immune | 1:20 | 203 | 268 | 132 |
|  |  | 1:40 | 210 | 275 | 135 |
|  |  | 1:80 | 205 | 265 | 129 |
| 919-CFA | Immune | 1:20 | 201 | 82 | 41 |
|  |  | 1:40 | 205 | 87 | 43 |
|  |  | 1:80 | 203 | 155 | 77 |

TABLE 2-continued

Bactericidal activity of 919 antigen using different adjuvant formulations

| Formulation | Pre-immune or immune | Sera dilution | Time 0 min | Time 60 min | % survival of MenB |
|---|---|---|---|---|---|
| 919-IFA | Pre-Immune | 1:20 | 206 | 265 | 128 |
|  |  | 1:40 | 210 | 280 | 133 |
|  |  | 1:80 | 211 | 295 | 139 |
| 919-IFA | Immune | 1:20 | 216 | 170 | 78 |
|  |  | 1:40 | 201 | 65 | 32 |
|  |  | 1:80 | 195 | 126 | 65 |
| 919-Alum | Pre-Immune | 1:20 | 196 | 270 | 137 |
|  |  | 1:40 | 210 | 285 | 135 |
|  |  | 1:80 | 206 | 294 | 142 |
| 919-Alum | Immune | 1:20 | 211 | 161 | 76 |
|  |  | 1:40 | 204 | 160 | 77 |
|  |  | 1:80 | 208 | 162 | 78 |
| 919-MF59 | Pre-immune | 1:20 | 205 | 270 | 131 |
|  |  | 1:40 | 215 | 271 | 126 |
|  |  | 1:80 | 198 | 268 | 135 |
| 919-MF59 | Immune | 1:20 | 200 | 120 | 60 |
|  |  | 1:40 | 201 | 121 | 60 |
|  |  | 1:80 | 196 | 119 | 60 |
| 919-CFA-oligo | Pre-immune | 1:20 | 205 | 271 | 132 |
|  |  | 1:40 | 204 | 264 | 129 |
|  |  | 1:80 | 210 | 279 | 132 |
| 919-CFA-oligo | Immune | 1:20 | 201 | 41 | 20 |
|  |  | 1:40 | 206 | 35 | 17 |
|  |  | 1:80 | 210 | 42 | 20 |

Example 6

Further Antigens

In addition to or instead of antigen '919' used in the above examples, the compositions of the invention can comprise one or more of the following protein antigens:
 a protein disclosed in WO99/57280, or an immunogenic fragment thereof;
 a protein disclosed in WO99/36544, or an immunogenic fragment thereof;
 a protein disclosed in WO99/24578, or an immunogenic fragment thereof;
 a protein disclosed in WO97/28273, or an immunogenic fragment thereof;
 a protein disclosed in WO96/29412, or an immunogenic fragment thereof;
 a protein disclosed in WO95/03413, or an immunogenic fragment thereof;
 a protein disclosed in WO99/31132, or an immunogenic fragment thereof;
 a protein disclosed in WO99/58683, or an immunogenic fragment thereof;
 a protein disclosed in WO99/55873, or an immunogenic fragment thereof; and/or
 a protein disclosed in GB-9928197.4, or an immunogenic fragment thereof.

If the composition comprises a protein disclosed in WO99/24578, said protein preferably comprises an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, & 892, as disclosed in WO99/24578 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO99/36544, said protein preferably comprises an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, & 90, as disclosed in WO99/36544 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO99/57280, said protein preferably comprises an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154; 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, 1164, 1166, 1168, 1170, 1172, 1174, 1176, 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, 1300, 1302, 1304, 1306, 1308, 1310, 1312, 1314, 1316, 1318, 1320, 1322, 1324, 1326, 1328, 1330, 1332, 1334, 1336, 1338, 1340, 1342, 1344, 1346, 1348, 1350, 1352, 1354, 1356, 1358, 1360, 1362, 1364, 1366, 1368, 1370, 1372, 1374, 1376, 1378, 1380, 1382, 1384, 1386, 1388, 1390, 1392, 1394, 1396, 1398, 1400, 1402, 1404, 1406, 1408, 1410, 1412, 1414, 1416, 1418, 1420, 1422, 1424, 1426, 1428, 1430, 1432, 1434, 1436, 1438, 1440, 1442, 1444, 1446, 1448, 1450, 1452, 1454, 1456, 1458, 1460, 1462, 1464, 1466, 1468, 1470, 1472, 1474, 1476, 1478, 1480, 1482, 1484, 1486, 1488, 1490, 1492, 1494, 1496, 1498, 1500, 1502, 1504, 1506, 1508, 1510, 1512, 1514, 1516, 1518, 1520, 1522, 1524, 1526, 1528, 1530, 1532, 1534, 1536, 1538, 1540, 1542, 1544, 1546, 1548, 1550, 1552, 1554, 1556, 1558, 1560, 1562, 1564, 1566, 1568, 1570, 1572, 1574, 1576, 1578, 1580, 1582, 1584, 1586, 1588, 1590, 1592, 1594, 1596, 1598, 1600, 1602, 1604, 1606, 1608, 1610, 1612, 1614, 1616, 1618, 1620, 1622, 1624, 1626, 1628, 1630, 1632, 1634, 1636, 1638, 1640, 1642, 1644, 1646, 1648, 1650, 1652, 1654, 1656, 1658, 1660, 1662, 1664, 1666, 1668, 1670, 1672, 1674, 1676, 1678, 1680, 1682, 1684, 1686, 1688, 1690, 1692, 1694, 1696, 1698, 1700, 1702, 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, 1760, 1762, 1764, 1766, 1768, 1770, 1772, 1774, 1776, 1778, 1780, 1782, 1784, 1786, 1788, 1790, 1792, 1794, 1796, 1798, 1800, 1802, 1804, 1806, 1808, 1810, 1812, 1814, 1816, 1818, 1820, 1822, 1824, 1826, 1828, 1830, 1832, 1834, 1836, 1838, 1840, 1842, 1844, 1846, 1848, 1850, 1852, 1854, 1856, 1858, 1860, 1862, 1864, 1866, 1868, 1870, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2030, 2032, 2034, 2036, 2038, 2040, 2042, 2044, 2046, 2048, 2050, 2052, 2054, 2056, 2058, 2060, 2062, 2064, 2066, 2068, 2070, 2072, 2074, 2076, 2078, 2080, 2082, 2084, 2086, 2088, 2090, 2092, 2094, 2096, 2098, 2100, 2102, 2104, 2106, 2108, 2110, 2112, 2114, 2116, 2118, 2120, 2122, 2124, 2126, 2128, 2130, 2132, 2134, 2136, 2138, 2140, 2142, 2144, 2146, 2148, 2150, 2152, 2154, 2156, 2158, 2160, 2162, 2164, 2166, 2168, 2170, 2172, 2174, 2176, 2178, 2180, 2182, 2184, 2186, 2188, 2190, 2192, 2194, 2196, 2198, 2200, 2202, 2204, 2206, 2208, 2210, 2212, 2214, 2216, 2218, 2220, 2222, 2224, 2226, 2228, 2230, 2232, 2234, 2236, 2238, 2240, 2242, 2244, 2246, 2248, 2250, 2252, 2254, 2256, 2258, 2260, 2262, 2264, 2266, 2268, 2270, 2272, 2274, 2276, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2324, 2326, 2328, 2330, 2332, 2334, 2336, 2338, 2340, 2342, 2344, 2346, 2348, 2350, 2352, 2354, 2356, 2358, 2360, 2362, 2364, 2366, 2368, 2370, 2372, 2374, 2376, 2378, 2380, 2382, 2384, 2386, 2388, 2390, 2392, 2394, 2396, 2398, 2400, 2402, 2404, 2406, 2408, 2410, 2412, 2414, 2416, 2418, 2420, 2422, 2424, 2426, 2428, 2430, 2432, 2434, 2436, 2438, 2440, 2442, 2444, 2446, 2448, 2450, 2452, 2454, 2456, 2458, 2460, 2462, 2464, 2466, 2468, 2470, 2472, 2474, 2476, 2478, 2480, 2482, 2484, 2486, 2488, 2490, 2492, 2494, 2496, 2498, 2500, 2502, 2504, 2506, 2508, 2510, 2512, 2514, 2516, 2518, 2520, 2522, 2524, 2526, 2528, 2530, 2532, 2534, 2536, 2538, 2540, 2542, 2544, 2546, 2548, 2550, 2552, 2554, 2556, 2558, 2560, 2562, 2564, 2566, 2568, 2570, 2572, 2574, 2576, 2578, 2580, 2582, 2584, 2586, 2588, 2590, 2592, 2594, 2596, 2598, 2600, 2602, 2604, 2606, 2608, 2610, 2612, 2614, 2616, 2618, 2620, 2622, 2624, 2626, 2628, 2630, 2632, 2634, 2636, 2638, 2640, 2642, 2644, 2646, 2648, 2650, 2652, 2654, 2656, 2658, 2660, 2662, 2664, 2666, 2668, 2670, 2672, 2674, 2676, 2678, 2680, 2682, 2684, 2686, 2688, 2690, 2692, 2694, 2696, 2698, 2700, 2702, 2704, 2706, 2708, 2710, 2712, 2714, 2716, 2718, 2720, 2722, 2724, 2726, 2728, 2730, 2732, 2734, 2736, 2738, 2740, 2742, 2744, 2746, 2748, 2750, 2752, 2754, 2756, 2758, 2760, 2762, 2764, 2766, 2768, 2770, 2772, 2774, 2776, 2778, 2780, 2782, 2784, 2786, 2788, 2790, 2792, 2794, 2796, 2798, 2800, 2802, 2804, 2806, 2808, 2810, 2812, 2814, 2816, 2818, 2820, 2822, 2824, 2826, 2828, 2830, 2832, 2834, 2836, 2838, 2840, 2842, 2844, 2846, 2848, 2850, 2852, 2854, 2856, 2858, 2860, 2862, 2864, 2866, 2868, 2870, 2872, 2874, 2876, 2878, 2880, 2882, 2884, 2886, 2888, 2890, 2892, 2894, 2896, 2898, 2900, 2902, 2904, 2906, 2908, 2910, 2912, 2914, 2916, 2918, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964, 2966, 2968, 2970, 2972, 2974, 2976, 2978, 2980, 2982, 2984, 2986, 2988, 2990, 2992, 2994, 2996, 2998, 3000, 3002, 3004, 3006, 3008, 3010, 3012, 3014, 3016, 3018 & 3020, as disclosed in WO99/57280 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO99/28273, said protein is preferably the protein disclosed in FIG. 4 or FIG. 13 of WO97/28273 (or a protein comprising an immunogenic fragment thereof or a protein comprising a sequence having sequence identity (preferably greater than 50% eg. 60%, 70%, 80%, 90%, 95%, 99% or more) thereto).

If the composition comprises a protein disclosed in WO96/29412, said protein preferably comprises an amino acid sequence selected from the group consisting of SEQ IDs 1-8 disclosed in WO96/29412 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO95/03413, said protein preferably comprises an amino acid sequence selected from the group consisting of SEQ IDs 1-23 disclosed in WO95/03413 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO99/31132, said protein preferably comprises an amino acid sequence selected from the group consisting of SEQ ID 2 disclosed in WO99/31132 (or a protein comprising an immunogenic fragment of SEQ ID 2, or a protein comprising a sequence having sequence identity (preferably greater than 50% eg. 60%, 70%, 80%, 90%, 95%, 99% or more) to SEQ ID 2).

If the composition comprises a protein disclosed in WO99/58683, said protein preferably comprises an amino acid sequence selected from the group consisting of SEQ ID 2 or SEQ ID 4 disclosed in WO99/58683 (or a protein comprising an immunogenic fragment of SEQ ID 2 or SEQ ID 4, or a protein comprising a sequence having sequence identity (preferably greater than 50% eg. 60%, 70%, 80%, 90%, 95%, 99% or more) to SEQ ID 2 or SEQ ID 4).

If the composition comprises a protein disclosed in WO99/55873, said protein preferably comprises an amino acid sequence selected from the group consisting of SEQ ID 2 or SEQ ID 4 disclosed in WO99/55873 (or a protein comprising an immunogenic fragment of SEQ ID 2 or SEQ ID 4, or a protein comprising a sequence having sequence identity (preferably greater than 50% eg. 60%, 70%, 80%, 90%, 95%, 99% or more) to SEQ ID 2 or SEQ ID 4).

If the composition comprises a protein disclosed in GB-9928197.4, said protein preferably comprises one of the following (i), (ii) or (iii):

(i) *N. meningitidis* serogroup B amino acid sequence (SEQ ID NO:32):

```
  1 MKLKQIASAL MMLGISPLAL ADFTIQDIRV EGLQRTEPST VFNYLPVKVG

51 DTYNDTHGSA IIKSLYATGF FDDVRVETAD GQLLLTVIER PTIGSLNITG

101 AKMLQNDAIK KNLESFGLAQ SQYFNQATLN QAVAGLKEEY LGRGKLNIQI

151 TPKVTKLARN RVDIDITIDE GKSAKITDIE FEGNQVYSDR KLMRQMSLTE

201 GGIWTWLTRS NQFNEQKFAQ DMEKVTDFYQ NNGYFDFRIL DTDIQTNEDK

251 TKQTIKITVH EGGRFRWGKV SIEGDTNEVP KAELEKLLTM KPGKWYERQQ

301 MTAVLGEIQN RMGSAGYAYS EISVQPLPNA ETKTVDFVLH IEPGRKIYVN

351 EIHITGNNKT RDEVVRRELR QMESAPYDTS KLQRSKERVE LLGYFDNVQF

401 DAVPLAGTPD KVDLNMSLTE RSTGSLDLSA GWVQDTGLVM SAGVSQDNLF
```

-continued

```
451 GTGKSAALRA SRSKTTLNGS LSFTDPYFTA DGVSLGYDVY GKAFDPRKAS

501 TSIKQYKTTT AGAGIRMSVP VTEYDRVNFG LVAEHLTVNT YNKAPKHYAD

551 FIKKYGKTDG TDGSFKGWLY KGTVGWGRNK TDSALWPTRG YLTGVNAEIA

601 LPGSKLQYYS ATHNQTWFFP LSKTFTLMLG GEVGIAGGYG RTKEIPFFEN

651 FYGGGLGSVR GYESGTLGPK VYDEYGEKIS YGGNKKANVS AELLFPMPGA

701 KDARTVRLSL FADAGSVWDG KTYDDNSSSA TGGRVQNIYG AGNTHKSTFT

751 NELRYSAGGA VTWLSPLGPM KFSYAYPLKK KPEDEIQRFQ FQLGTTF*
``` or a protein comprising an immunogenic fragment thereof, or a protein comprising a sequence having sequence identity (preferably greater than 50% eg. 60%, 70%, 80%, 90%, 95%, 99% or more) thereto. The protein may lack its signal peptide MKLKQIASALMMLGISPLALA;

(ii) *N. gonorrhoeae* amino acid sequence (SEQ ID NO:33):

```
  1 MKLKQIASAL MMLGISPLAF ADFTIQDIRV EGLQRTEPST VFNYLPVKVG

51 DTYNDTHGSA IIKSLYATGF FDDVRVETAD GQLLLTVIER PTIGSLNITG

101 AKMLQNDAIK KNLESFGLAQ SQYFNQATLN QAVAGLKEEY LGRGKLNIQI

151 TPKVTKLARN RVDIDITIDE GKSAKITDIE FEGNQVYSDR KLMRQMSLTE

201 GGIWTWLTRS DRFDRQKFAQ DMEKVTDFYQ NNGYFDFRIL DTDIQTNEDK

251 TRQTIKITVH EGGRFRWGKV SIEGDTNEVP KAELEKLLTM KPGKWYERQQ

301 MTAVLGEIQN RMGSAGYAYS EISVQPLPNA GTKTVDFVLH IEPGRKIYVN

351 EIHITGNNKT RDEVVRRELR QMESAPYDTS KLQRSKERVE LLGYFDNVQF

401 DAVPLAGTPD KVDLNMSLTE RSTGSLDLSA GWVQDTGLVM SAGVSQDNLF

451 GTGKSAALRA SRSKTTLNGS LSFTDPYFTA DGVSLGYDIY GKAFDPRKAS

501 TSVKQYKTTT AGGGVRMGIP VTEYDRVNFG LAAEHLTVNT YNKAPKRYAD

551 FIRKYGKTDG ADGSFKGLLY KGTVGWGRNK TDSASWPTRG YLTGVNAEIA

601 LPGSKLQYYS ATHNQTWFFP LSKTFTLMLG GEVGIAGGYG RTKEIPFFEN

651 FYGGGLGSVR GYESGTLGPK VYDEYGEKIS YGGNKKANVS AELLFPMPGA

701 KDARTVRLSL FADAGSVWDG RTYTAAENGN NKSVYSENAH KSTFTNELRY

751 SAGGAVTWLS PLGPMKFSYA YPLKKKPEDE IQRFQFQLGT TF*
``` or a protein comprising an immunogenic fragment thereof, or a protein comprising a sequence having sequence identity (preferably greater than 50% eg. 60%, 70%, 80%, 90%, 95%, 99% or more) thereto. The protein may lack its signal peptide MKLKQIASALMMLGISPLAFA;

(iii) *N. meningitidis* serogroup A amino acid sequence (SEQ ID NO:34):

```
  1 MKLKQIASAL MVLGISPLAL ADFTIQDIRV EGLQRTEPST VFNYLPVKVG

51 DTYNDTHGSA IIKSLYATGF FDDVRVETAD GQLLLTVIER PTIGSLNITG

101 AKMLQNDAIK KNLESFGLAQ SQYFNQATLN QAVAGLKEEY LGRGKLNIQI

151 TPKVTKLARN RVDIDITIDE GKSAKITDIE FEGNQVYSDR KLMRQMSLTE

201 GGIWTWLTRS NQFNEQKFAQ DMEKVTDFYQ NNGYFDFRIL DTDIQTNEDK

251 TKQTIKITVH EGGRFRWGKV SIEGDTNEVP KAELEKLLTM KPGKWYERQQ

301 MTAVLGEIQN RMGSAGYAYS EISVQPLPNA ETKTVDFVLH IEPGRKIYVN

351 EIHITGNNKT RDEVVRRELR QMESAPYDTS KLQRSKERVE LLGYFDNVQF
```

```
401 DAVPLAGTPD KVDLNMSLTE RSTGSLDLSA GWVQDTGLVM SAGVSQDNLF

451 GTGKSAALRA SRSKTTLNGS LSFTDPYFTA DGVSLGYDVY GKAFDPRKAS

501 TSIKQYKTTT AGAGIRMSVP VTEYDRVNFG LVAEHLTVNT YNKAPKHYAD

551 FIKKYGKTDG TDGSFKGWLY KGTVGWGRNK TDSALWPTRG YLTGVNAEIA

601 LPGSKLQYYS ATHNQTWFFP LSKTFTLMLG GEVGIAGGYG RTKEIPFFEN

651 FYGGGLGSVR GYESGTLGPK VYDEYGEKIS YGGNKKANVS AELLFPMPGA

701 KDARTVRLSL FADAGSVWDG KTYDDNSSSA TGGRVQNIYG AGNTHKSTFT

751 NELRYSAGGA VTWLSPLGPM KFSYAYPLKK KPEDEIQRFQ FQLGTTF*
``` or a protein comprising an immunogenic fragment thereof, or a protein comprising a sequence having sequence identity (preferably greater than 50% eg. 60%, 70%, 80%, 90%, 95%, 99% or more) thereto. The protein may lack its signal peptide MKLKQIASALMVLGISPLALA.

Preferred proteins for use as the Neisserial antigen are:
protein '919', typified by SEQ IDs 3069-3074 and 3207-3241 of WO99/57280 (see also FIG. 23 and Example 15 therein).
protein '235', typified by SEQ IDs 869-874 and 3149-3178 of WO99/57280 (see also FIG. 20 and Example 12 therein).
protein '519', typified by SEQ IDs 3045-3056 and 3185-3206 of WO99/57280 (see also FIG. 22 and Example 14 therein).
protein '225', typified by SEQ IDs 793-804 and 3115-3148 of WO99/57280 (see also FIG. 19 and Example 11 therein).
protein 'ORF40', typified by example 1 (SEQ IDs 1-6) of WO99/36544 (see also FIG. 1 of GB-9910168.5; see also WO99/31132 and WO99/58683).
protein 'ORF4', typified by example 26 (SEQ IDs 215-226) of WO99/24578 (see also FIG. 2 of GB-9910168.5).

It will be understood that this application describes the invention by way of example only and modifications may be made whilst remaining within the scope and spirit of the invention.

---

The invention claimed is:

1. An immunogenic composition comprising:
   (a) an immunostimulating amount of a *Neisseria* antigen; and
   (b) an immunostimulating amount of an adjuvant composition comprising:
      (i) an oligonucleotide comprising at least one CG motif; and
      (ii) an emulsion comprising submicron oil droplets and an emulsifying agent,
   wherein the ratio of the emulsifying agent to the oil in said emulsion allows production of an emulsion wherein at least 80% of said oil droplets are less than 1 micron in diameter and wherein the oligonucleotide is at least 6 nucleotides and less than 100 nucleotides in length and comprises at least one phosphorothioate bond and the CG motif comprises an unmethylated CpG dinucleotide.

2. The composition of claim 1, wherein said *Neisseria* antigen is selected from the group consisting of a protein, protein-polysaccharide, protein-lipopolysaccharide, polysaccharide, and lipopolysaccharide.

3. The composition of claim 1 or claim 2, wherein said *Neisseria* antigen is from *Neisseria meningitidis* or *Neisseria gonorrhoeae*.

4. The composition of claim 3 wherein said *Neisseria* antigen is a *Neisseria meningitidis* serogroup B peptide.

5. The composition of claim 1, wherein component (b) further comprises a second adjuvant.

6. The composition of claim 1, wherein said emulsion comprises a metabolizable oil.

7. The composition of claim 6, wherein said emulsion exists in the absence of any polyoxypropylene-polyoxyethylene block copolymer.

8. The composition of claim 7, wherein said oil is an animal oil, an unsaturated hydrocarbon, a vegetable oil, or a terpenoid.

9. The composition of claim 8 wherein said terpenoid is squalene.

10. The composition of claim 9, wherein said composition comprises 0.5 to 20% by volume of said oil in an aqueous medium.

11. The composition of claim 9, wherein said emulsifying agent comprises a non-ionic detergent or a polyoxyethylene sorbitan mono-, di-, or triester or a sorbitan mono-, di-, or triether.

12. The composition of claim 9, wherein said composition comprises 0.01 to 0.5% by weight of said emulsifying agent.

13. The composition claim 1, further comprising a separate immunostimulating agent.

14. The composition of claim 13 wherein said immunostimulating agent is selected from the group consisting of a bacterial cell wall component and muramyl peptide.

15. The composition of claim 5, wherein said second adjuvant comprises alum, incomplete Freund's adjuvant (IFA), or complete Freund's adjuvant (CFA).

16. The composition of claim 1, wherein said oligonucleotide comprises at least one phosphorothioate bond.

17. The composition of claim 1, wherein said oligonucleotide comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, and SEQ ID NO: 27.

18. The composition of claim 1, wherein said oligonucleotide comprises a CG motif flanked by two purines immediately 5' to said motif and two pyrimidines immediately 3' to said motif.

19. The composition of claim 18, wherein said oligonucleotide comprises a nucleotide sequence selected from the group consisting of SEQ ID NO: 1, SEQ ID NO: 2, SEQ ID NO: 3, SEQ ID NO: 7, SEQ ID NO: 8, SEQ ID NO: 9, SEQ ID NO: 12, SEQ ID NO: 13, SEQ ID NO: 19, SEQ ID NO: 20, SEQ ID NO: 21, SEQ ID NO: 22, SEQ ID NO: 23, SEQ ID NO: 24, and SEQ ID NO: 25.

20. A vaccine composition comprising:
a) an immunostimulating amount of a *Neisseria meningitidis* serogroup B antigen; and
b) an immunostimulating amount of an adjuvant composition comprising:
(i) an oligonucleotide comprising at least one CG motif; and
(ii) an emulsion comprising submicron oil droplets and an emulsifying agent, wherein the ratio of the emulsifying agent to the oil in said emulsion allows production of an emulsion wherein at least 80% of said oil droplets are less than 1 micron in diameter and wherein the oligonucleotide is at least 6 nucleotides and less than 100 nucleotides in length and comprises at least one phosphorothioate bond and the CG motif comprises an unmethylated CpG dinucleotide.

21. The vaccine composition of claim 20, wherein component (b) further comprises a second adjuvant.

22. A method of stimulating an immune response in a host animal comprising administering to said animal a composition of claim 1 in an amount effective to induce an immune response.

23. The method of claim 22 wherein said host animal is a mammal.

24. A method of immunizing a host animal against *Neisseria* infection comprising administering to said animal a composition of claim 20 in an amount effective to induce a protective response.

25. The method of claim 24 wherein said host animal is a mammal.

26. The method of claim 25 wherein said mammal is a human.

27. A method of immunizing a host animal against *Neisseria meningitidis* comprising administering to said animal a composition of claim 20 in an amount effective to induce a protective response, wherein said antigen is a *Neisseria meningitidis* group B peptide.

28. The method of claim 27 wherein said peptide comprises SEQ ID NO: 31.

29. The method of claim 28 wherein said host animal is a human.

30. The composition of claim 10, wherein the emulsifying agent comprises a non-ionic detergent or a polyoxyethylene sorbitan mono-, di-, or triester or a sorbitan mono-, di-, or triether.

31. The composition of claim 10, wherein said composition comprises 0.01 to 0.5% by weight of said emulsifying agent.

32. The composition of claim 11, wherein said composition comprises 0.01 to 0.5% by weight of said emulsifying agent.

33. An immunogenic composition comprising:
(a) an immunostimulating amount of a *Neisseria meningitidis* serogroup B antigen comprising SEQ ID NO: 31; and
(b) an immunostimulating amount of an adjuvant composition comprising:
(i) an oligonucleotide comprising at least one CG motif; and
(ii) an emulsion comprising submicron oil droplets and an emulsifying agent, wherein the ratio of the emulsifying agent to the oil in said emulsion allows production of an emulsion wherein at least 80% of said oil droplets are less than 1 micron in diameter and wherein the oligonucleotide wherein the oligonucleotide is at least 6 nucleotides and less than 100 nucleotides in length and comprises at least one phosphorothioate bond and the CG motif comprises an unmethylated CpG dinucleotide.

34. A vaccine composition comprising:
a) an immunostimulating amount of a *Neisseria meningitidis* serogroup B antigen comprising SEQ ID NO: 31; and
b) an immunostimulating amount of an adjuvant composition comprising:
(i) an oligonucleotide comprising at least one CG motif; and
(ii) an emulsion comprising submicron oil droplets and an emulsifying agent, wherein the ratio of the emulsifying agent to the oil in said emulsion allows production of an emulsion wherein at least 80% of said oil droplets are less than 1 micron in diameter and wherein the oligonucleotide is at least 6 nucleotides and less than 100 nucleotides in length and comprises at least one phosphorothioate bond and the CG motif comprises an unmethylated CpG dinucleotide.

35. A vaccine composition of claim 34, wherein component (b) further comprises a second adjuvant.

* * * * *